United States Patent [19]
Patane et al.

[11] Patent Number: 6,057,350
[45] Date of Patent: *May 2, 2000

[54] ALPHA 1A ADRENERGIC RECEPTOR ANTAGONISTS

[75] Inventors: Michael A. Patane, Harleysville; Mark G. Bock, Hatfield, both of Pa.; Dhanapalan Nagarathnam, Ramsey, N.J.; Bharat Lagu, Maywood, N.J.; Wai C. Wong, Newark, N.J.

[73] Assignees: Merck & Co., Inc., Rahway; Synaptic Pharmaceutical Corp., Paramus, both of N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/098,781

[22] Filed: Jun. 17, 1998

(Under 37 CFR 1.47)

Related U.S. Application Data

[60] Provisional application No. 60/050,136, Jun. 18, 1997.
[51] Int. Cl.$^7$ .......................... A61K 31/42; A61K 31/425; C07D 263/22; C07D 275/06
[52] U.S. Cl. .......................... 514/376; 514/373; 514/523; 548/210; 548/211; 548/229; 548/230; 558/426
[58] Field of Search .................................. 548/229, 230; 514/376

[56] References Cited

U.S. PATENT DOCUMENTS

| | | | |
|---|---|---|---|
| 3,193,559 | 7/1965 | Regnier et al. | 260/307 |
| 4,593,042 | 6/1986 | Liang | 514/523 |
| 4,661,491 | 4/1987 | Regnier | 514/260 |
| 4,769,371 | 9/1988 | Atwal | 544/58.5 |
| 4,847,379 | 7/1989 | Atwal | 544/316 |
| 4,855,301 | 8/1989 | Atwal et al. | 514/269 |
| 5,202,330 | 4/1993 | Atwal et al. | 514/274 |
| 5,231,179 | 7/1993 | Terashima et al. | 540/200 |
| 5,380,737 | 1/1995 | Dunlap et al. | 514/373 |

FOREIGN PATENT DOCUMENTS

| | | |
|---|---|---|
| 0 234 830 | 9/1987 | European Pat. Off. . |
| 0 236 902 | 9/1987 | European Pat. Off. . |
| 1329617 | 5/1963 | France . |
| 92/00073 | 1/1992 | WIPO . |
| 92/16213 | 10/1992 | WIPO . |
| 94/08040 | 4/1994 | WIPO . |
| 94/10989 | 5/1994 | WIPO . |
| 94/22829 | 10/1994 | WIPO . |
| 96/14846 | 5/1996 | WIPO . |
| 97/17969 | 5/1997 | WIPO . |
| 97/42956 | 11/1997 | WIPO . |

OTHER PUBLICATIONS

W. C. Wong et al., "Design and Synthesis of Dihydropyrimidines as Alpha 1a Adrenoceptor Selective Antagonists", Abstract No. MEDI 064, 215th ACS National Meeting, Dallas, TX (Mar. 29–Apr. 2, 1998).

B. Lagu et al., "Design, Synthesis and Evaluation of Dihydropyrimidinones as Alpha 1a Selective Antagonists", Abstract No, MEDI 065, 215th ACS National Meeting, Dallas, TX (Mar. 29–Apr. 2, 1998).

D. Nagarathnam et al., "Design, Synthesis and Evaluation of Dihydropyrimidinones as Alpha 1a Selective Antagonists: 6, Synthesis and Structure–Activity Relationship of SNAP 6553 and Analogs", Abstract No. MEDI 066, 215th ACS National Meeting, Dallas, TX (Mar.–Apr. 2, 1998).

M. R. Marzabadi et al, "Design, Synthesis and Evaluation of Dihydropyrimidinones and Dihydropyrimidines as Alpha 1a Selective Antagonists: Modification of the Diarylpiperidine Moiety", Abstract No. MEDI 067, 215th ACS National Meeting, Dallas, TX (Mar. 29–Apr. 2, 1998).

Derwent CPI Abstracts No. 90–041598, "Remedy for Dysuria", Abstract of JP01–319418, Nippon Chemifar (1990).

Derwent CPI Abstracts No. 87–027600, "New 1,3–oxazolidin–2–one derivatives", Abstract of JP61–286375, Nippon Chemifar (1987).

G. C. Rovnyak et al., "Dihydropyrimidine Calcium Channel Blockers. 4. Basic 3–Substitutued–4–aryl–1,4–dihydropyrimidine–5–carboxylic Acid Esters. Potent Antihypertensive Agents", J. Med. Chem., 35(17), 3254–63 (1992).

K. S. Atwal et al., "Dihydropyrimidine Calcium Channel Blockers. 3. 3–Carbamoyl–4–aryl–1,2,3,4–tetrahydro–6–methyl–5–pyrimidinecarboxylic Acid Esters as Orally Effective Antihypertensive Agents", J. Med. Chem., 34(2), 806–11 (1991).

K. S. Atwal et al., "Dihydropyrimidine Calcium Channel Blockers. 2. 3–Substituted–4–aryl–1,4–dihydro–6–methyl–5–pyrimidinecarboxylic Acid Esters as Potent Mimics of Dihydropyridines", J. Med. Chem., 33(9), 2629–35 (1990).

K. S. Atwal et al., "Substituted 1,4–Dihydropyrimidines. 3. Synthesis of Sellectively Functionalized 2–Hetero–1,4–dihydropyrimidines", J. Org. Chem., 54(25), 5898–907 (1989).

*Primary Examiner*—Laura L. Stockton
*Attorney, Agent, or Firm*—Kenneth R. Walton; Melvin Winokur

[57] ABSTRACT

This invention relates to certain novel compounds and derivatives thereof, their synthesis, and their use as alpha 1*a* adrenergic receptor antagonists. One application of these compounds is in the treatment of benign prostatic hyperplasia. These compounds are selective in their ability to relax smooth muscle tissue enriched in the alpha 1*a* receptor subtype without at the same time inducing hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia are achieved.

24 Claims, No Drawings

ALPHA 1A ADRENERGIC RECEPTOR ANTAGONISTS

This application claims the benefit of U.S. Provisional Application No. 60/050,136, filed Jun. 18, 1997.

FIELD OF THE INVENTION

This invention relates to certain novel compounds and derivatives thereof, their synthesis, and their use as alpha 1a adrenoceptor antagonists. More particularly, the compounds of the present invention are useful for treating benign prostatic hyperplasia (BPH).

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, β1, and β2 subtypes. Functional differences between alpha 1 and alpha 2 receptors have been recognized, and compounds which exhibit selective binding between these two subtypes have been developed.

For a general background on the alpha adrenergic receptors, the reader's attention is directed to Robert R. Ruffolo, Jr., α-*Adrenoreceptors: Molecular Biology, Biochemistry and Pharmacology*, (*Progress in Basic and Clinical Pharmacology* series, Karger, 1991), wherein the basis of alpha 1/alpha 2 subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting alpha-adrenergic receptor affinity was explored.

The cloning, sequencing and expression of alpha receptor subtypes from animal tissues has led to the subclassification of the alpha 1 receptors into alpha 1d (formerly known as alpha 1a or 1a/1d), alpha 1b and alpha 1a (formerly known as alpha 1c) subtypes. Each alpha 1 receptor subtype exhibits its own pharmacologic and tissue specificities. The designation "alpha 1a" is the appellation recently approved by the IUPHAR Nomenclature Committee for the previously designated "alpha 1c" cloned subtype as outlined in the 1995 Receptor and Ion Channel Nomenclature Supplement (Watson and Girdlestone, 1995). The designation alpha 1a is used throughout this application to refer to this subtype. At the same time, the receptor formerly designated alpha 1a was renamed alpha 1d. The new nomenclature is used throughout this application. Stable cell lines expressing these alpha 1 receptor subtypes are referred to herein; however, these cell lines were deposited with the American Type Culture Collection (ATCC) under the old nomenclature. For a review of the classification of alpha 1 adrenoceptor subtypes, see, Martin C. Michel, et al., *Naunyn-Schmiedeberg's Arch. Pharmacol.* (1995) 352:1–10.

The differences in the alpha adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concommitantly, the increased noradrenergic innervation of the enlarged prostate leads to an increased adrenergic tone of the bladder neck and urethra, further restricting the flow of urine through the urethra.

In benign prostatic hyperplasia, the male hormone 5alpha-dihydrotestosterone has been identified as the principal culprit. The continual production of 5α-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc.s' product PROSCAR® (finasteride). The effect of this compound is to inhibit the enzyme testosterone 5α-reductase, which converts testosterone into 5α-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the lower urinary tract tissue, by binding to alpha 1 adrenergic receptors, thus reducing the increased adrenergic tone due to the disease, would be good candidates for this activity. Thus, one such agent is alfuzosin, which is reported in EP 0 204597 to induce urination in cases of prostatic hyperplasia. Likewise, in WO 92/0073, the selective ability of the R(+) enantiomer of terazosin to bind to adrenergic receptors of the alpha$_1$ subtype was reported. In addition, in WO 92/161213, combinations of 5α-reductase inhibitory compounds and alpha1-adrenergic receptor blockers (terazosin, doxazosin, prazosin, bunazosin, indoramin, alfuzosin) were disclosed. However, no information as to the alpha 1d, alpha 1b, or alpha 1a subtype specificity of these compounds was provided as this data and its relevancy to the treatment of BPH was not known. Current therapy for BPH uses existing non-selective alpha 1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha 1d and alpha 1b receptors in the peripheral vasculature, e.g., hypotension and syncope.

The recent cloning of the human alpha 1a adrenergic receptor (ATCC CRL 11140) and the use of a screening assay utilizing the cloned human alpha 1a receptor enables identification of compounds which specifically interact with the human alpha 1a adrenergic receptor. [PCT International Application Publication Nos. WO94/08040, published Apr. 14, 1994 and WO94/10989, published May 26, 1994] As disclosed in the instant patent disclosure, a cloned human alpha 1a adrenergic receptor and a method for identifying compounds which bind the human alpha 1a receptor has now made possible the identification of selective human alpha 1a adrenergic receptor antagonists useful for treating BPH. The instant patent disclosure discloses novel compounds which selectively bind to the human alpha 1a receptor. These compounds are further tested for binding to other human alpha 1 receptor subtypes, as well as counter-screened against other types of receptors (e.g., alpha 2), thus defining the specificity of the compounds of the present invention for the human alpha 1a adrenergic receptor.

It is an object of the present invention to identify compounds which bind to the alpha 1a adrenergic receptor. It is a further object of the invention to identify compounds which act as antagonists of the alpha 1a adrenergic receptor. It is another object of the invention to identify alpha 1a adrenergic receptor antagonist compounds which are useful agents for treating BPH in animals, preferably mammals, especially humans. Still another object of the invention is to identify alpha 1a adrenergic receptor antagonists which are useful for relaxing lower urinary tract tissue in animals, preferably mammals, especially humans.

It has now been found that the compounds of the present invention are alpha 1a adrenergic receptor antagonists. Thus, the compounds of the present invention are useful for treating BPH in mammals. Additionally, it has been found that the alpha 1a adrenergic receptor antagonists of the present invention are also useful for relaxing lower urinary tract tissue in mammals.

SUMMARY OF THE INVENTION

The present invention provides compounds for the treatment of urinary obstruction caused by benign prostatic hyperplasia (BPH). The compounds antagonize the human alpha 1a adrenergic receptor at nanomolar and subnanomolar concentrations while exhibiting at least ten fold lower affinity for the alpha 1d and alpha 1b human adrenergic receptors and many other G-protein coupled receptors. This invention has the advantage over non-selective alpha 1 adrenoceptor antagonists of reduced side effects related to peripheral adrenergic blockade. Such side effects include hypotension, syncope, lethargy, etc. The compounds of the present invention have the structure:

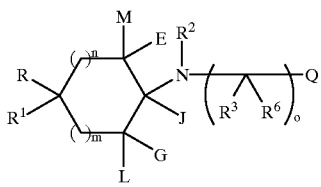

wherein Q is selected from

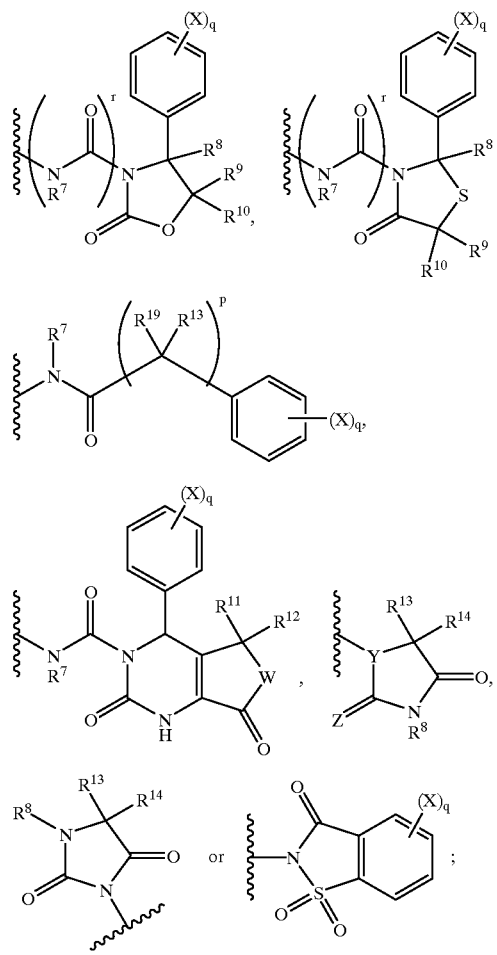

E, G, L and M are each independently selected from hydrogen, $C_{1-8}$ alkyl, $C_{3-8}$ cycloalkyl, $(CH_2)_{0-4}OR^{15}$, $(CH_2)_{0-4}N(R^{16})_2$, $(CH_2)_{0-4}CN$, $(CH_2)_{0-4}CF_3$, $(CH_2)_{0-4}CO_2R^{16}$, $(CH_2)_{0-4}CON(R^{16})_2$, $(CH_2)_{0-4}SO_2R^{15}$ or $(CH_2)_{0-4}SO_2N(R^{16})_2$;

J is selected from hydrogen, $C_{1-8}$ alkyl, $C_{3-8}$ cycloalkyl, $(CH_2)_{1-4}OR^{15}$, $(CH_2)_{1-4}N(R^{16})_2$, $(CH_2)_{1-4}CN$, $(CH_2)_{0-4}CF_3$, $(CH_2)_{0-4}CO_2R^{16}$, $(CH_2)_{0-4}CON(R^{16})_2$, $(CH_2)_{0-4}SO_2R^{15}$ or $(CH_2)_{0-4}SO_2N(R^{16})_2$;

$R^1$ is selected from unsubstituted, mono- or poly-substituted phenyl wherein the substitutents on the phenyl are independently selected from halogen, $CF_3$, cyano, nitro, $N(R^{16})_2$, $NR^{16}COR^{18}$, $NR^{16}CON(R^{18})_2$, $NR^{16}SO_2R^{18}$, $NR^{16}SO_2N(R^{18})_2$, $OR^{15}$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$ or $C_{1-4}$ alkyl; or unsubstituted, mono- or poly-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, nitro, $N(R^{16})_2$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$, phenyl, $OR^{15}$, halogen, $C_{1-4}$ alkyl or $_{3-8}$ cycloalkyl;

R is selected from hydrogen, cyano, $OR^{15}$, $CO_2R^{15}$, $CON(R^{16})_2$, $SO_2R^{15}$, $SO_2N(R^{16})_2$, tetrazole, isooxadiazole, unsubstituted, mono- or poly-substitued phenyl wherein the substitutents on the phenyl are independently selected from halogen, cyano, $OR^{15}$, $(CH_2)_{0-4}CO_2R^{16}$, $(CH_2)_{0-4}CON(R^{16})_2$, $N(R^{16})_2$, $NR^{16}COR^{15}$, $NR^{16}CON(R^{18})_2$, $NR^{16}SO_2R_{15}$, $NR^{16}SO_2N(R^{18})_2$, $(CH_2)_{0-4}SO_2N(R^{16})_2$, $(CH_2)_{0-4}SO_2R^{15}$ or $C_{1-4}$ alkyl; or unsubstituted, mono- or poly-substituted pyridyl, thienyl, furanyl or naphthyl wherein the substituents on the pyridyl, thienyl, furanyl or naphthyl are independently selected from $CF_3$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$, phenyl, $OR^{15}$, halogen, $C_{1-4}$ alkyl or $C_{3-8}$ cycloalkyl;

$R^2$ and $R^7$ are each independently selected from hydrogen, $C_{1-8}$ alkyl, $C_{4-8}$ cycloalkyl, $(CH_2)_{0-4}CO_2R^{16}$, $(CH_2)_{0-4}CON(R^{16})_2$, $(CH_2)_{0-4}COR^{15}$, $(CH_2)_{2-4}OR^{15}$, $(CH_2)_{1-4}CF_3$, $(CH_2)_{0-4}SO_2R^{15}$, $(CH_2)_{0-4}SO_2N(R^{16})_2$ or $(CH_2)_{1-4}CN$;

$R^3$, $R^6$, $R^8$, $R^9$ and $R^{10}$ are each independently selected from hydrogen, $C_{1-8}$ alkyl, $C_{3-8}$ cycloalkyl, $(CH_2)_{1-4}OR^{15}$ or $(CH_2)_{0-4}CF_3$;

$R^{11}$ and $R^{12}$ are each independently selected from hydrogen, $C_{1-8}$ alkyl or $C_{3-8}$ cycloalkyl;

$R^{13}$ and $R^{14}$ are each independently selected from hydrogen, $C_{1-8}$ alkyl, $C_{3-8}$ cycloalkyl, $(CH_2)_{0-4}OR^{15}$, $(CH_2)_{0-4}CF_3$, unsubstituted, mono- or independently selected from halogen, CF3, cyano, nitro, $CO_2R^{16}$, $OR^{15}$, independently selected from halogen, $CF_3$, cyano, nitro, $CO_2R^{16}$, $OR^{15}$, $(CH_2)_{0-4}CON(R^{16})_2$, $(CH_2)_{0-4}CO_2R^{16}$ or $C_{1-4}$ alkyl; or unsubstituted, mono- or poly-substituted: pyridyl, thienyl, furanyl or naphthyl are independently selected from $CF_3$, phenyl, $OR^{15}$, furanyl or naphthyl are independently selected from $CF_3$, phenyl, $OR^{15}$, halogen, $C_{1-4}$ alkyl or $C_{3-8}$ cycloalkyl;

$R^{15}$ is selected from hydrogen, $C_{1-8}$ alkyl, $C_{3-8}$ cycloalkyl or $(CH_2)_{0-4}CF_3$;

$R^{16}$ and $R^{18}$ are each independently selected from hydrogen, $C_{1-8}$ alkyl, $C_{3-8}$ cycloalkyl or $(CH_2)_{1-4}CF_3$;

$R^{19}$ is selected from hydrogen, $C_{1-8}$ alkyl, $C_{3-8}$ cycloalkyl, $(CH_2)_{0-4}OR^{15}$ or $(CH_2)_{0-4}CF_3$;

W is O or $NR^{11}$;

each X is independently selected from halogen, cyano, nitro, $C_{1-8}$ alkyl, $C_{3-8}$ cycloalkyl, $(CH_2)_{0-4}OR^{24}$ or $(CH_2)_{0-4}CF_3$;

$R^{24}$ is selected from hydrogen, $C_{1-8}$ alkyl, $C_{3-8}$ cycloalkyl or $(CH_2)_{0-4}CF_3$;

Y is $C-R^{15}$ or N;

Z is hydrogen, oxygen or sulphur;

m, n, p and q are each independently an integer from zero to four;

o is an integer from one to four;

r is zero or one;

and the pharmaceutically acceptable salts thereof.

In one embodiment of the invention is the compound of the formula

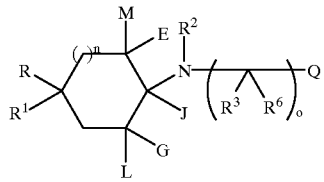

wherein E, G, L, M and J are each independently selected from hydrogen, $C_{1-8}$ alkyl, $C_{3-8}$ cycloalkyl, $(CH_2)_{0-4}CO_2R^{16}$ or $(CH_2)_{0-4}CF_3$;

$R^1$ is selected from unsubstituted, mono-, di- or tri-substituted phenyl wherein the substitutents on the phenyl are independently selected from halogen, $CF_3$, cyano, nitro, $N(R^{16})_2$, $NR^{16}COR^{18}$, $NR^{16}CON(R^{18})_2$, $NR^{16}SO_2R^{18}$, $NR^{16}SO_2N(R^{18})_2$, $OR^{15}$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2(R^{15})_2$ or $C_{1-4}$ alkyl; or unsubstituted, mono-, di- or tri-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, nitro, $N(R^{16})_2$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2(R^{15})_2$, phenyl, $OR^{15}$, halogen, $C_{1-4}$ alkyl or $C_{3-8}$ cycloalkyl;

R is selected from hydrogen, cyano, $OR^{15}$, $CO_2R^{15}$, $CON(R^{16})_2$, $SO_2R^{15}$, $SO_2N(R^{16})_2$ or unsubstituted, mono- or di-substituted phenyl wherein the substitutents on the phenyl are independently selected from halogen, cyano, $OR^{15}$, $(CH_2)_{0-4}CO_2R^{16}$, $(CH_2)_{0-4}CON(R^{16})_2$, $N(R^{16})_2$, $NR^{16}COR^{15}$, $NR^{16}CON(R^{18})_2$, $NR^{16}SO_2R_{15}$, $NR^{16}SO_2N(R^{18})_2$, $(CH_2)_{0-4}SO_2N(R^{16})_2$, $(CH_2)_{0-4}SO_2R^{15}$ or $C_{1-4}$ alkyl; or unsubstituted, mono- or di-substituted pyridyl, thienyl, furanyl or naphthyl wherein the substituents on the pyridyl, thienyl, furanyl or naphthyl are independently selected from $CF_3$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$, phenyl, $OR^{15}$, halogen, $C_{1-4}$ alkyl or $C_{3-8}$ cycloalkyl;

$R^2$ and $R^7$ are each independently selected from hydrogen, $C_{1-8}$ alkyl, $C_{4-8}$ cycloalkyl or $(CH_2)_{1-4}CF_3$;

$R^{13}$ and $R^{14}$ are each independently selected from hydrogen, $C_{1-8}$ alkyl, $C_{3-8}$ cycloalkyl, $(CH_2)_{1-4}OR^{15}$, $(CH_2)_{0-4}CF_3$, unsubstituted, mono-, di- or tri-substituted phenyl wherein the substituents on the phenyl are independently selected from halogen, $CF_3$, cyano, nitro, $CO_2R^{16}$, $OR^{15}$, $(CH_2)_{0-4}CON(R^{16})_2$, $(CH_2)_{0-4}CO_2R^{16}$ or $C_{1-4}$ alkyl; or unsubstituted, mono-, di- or tri-substituted: pyridyl, thienyl, furanyl or naphthyl wherein the substituents on the pyridyl, thienyl, furanyl or naphthyl are independently selected from $CF_3$, phenyl, $OR^{15}$, halogen, $C_{1-4}$ alkyl or $C_{3-8}$ cycloalkyl;

n is an integer from zero to two;

o is an integer from one to four;

and all other variables are as defined previously;

and the pharmaceutically acceptable salts thereof

In a class of the invention is the compound of the formula

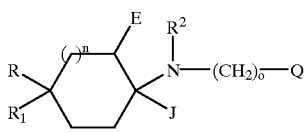

wherein Q is selected from

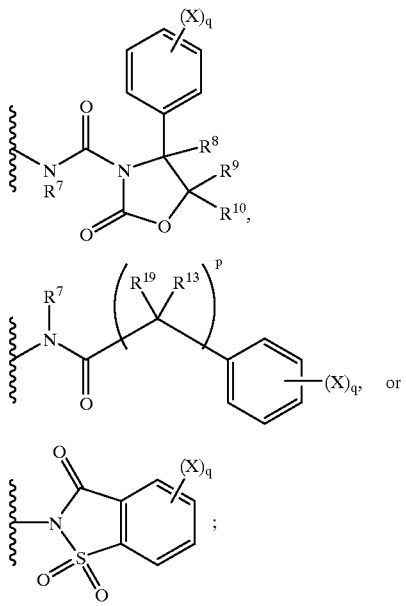

E and J are each independently selected from hydrogen or $CO_2$—$C_{1-6}$ alkyl;
$R^1$ is selected from unsubstituted, mono-, di- or tri-substituted phenyl wherein the substitutents on the phenyl are independently selected from halogen, $CF_3$, cyano, nitro, $N(R^{16})_2$, $OR^{15}$, $(CH_2)_{0-2}CO_2R^{16}$, $(CH_2)_{0-2}CON(R^{16})_2$ or $C_{1-4}$ alkyl; or unsubstituted, mono- or di-substituted pyridyl wherein the substitutents on the pyridyl are independently selected from halogen, $CF_3$, cyano, nitro, $N(R^{16})_2$, $OR^{15}$, $(CH_2)_{0-2}CO_2R^{16}$, $(CH_2)_{0-2}CON(R^{16})_2$ or $C_{1-4}$ alkyl;
R is selected from hydrogen, cyano, $OR^{15}$, $CO_2R^{15}$, $CON(R^{16})_2$, $SO_2R^{15}$ or $SO_2N(R^{16})_2$;
$R^2$ and $R^7$ are each independently selected from hydrogen, $C_{1-6}$ alkyl, $C_{4-6}$ cycloalkyl or $(CH_2)_{1-4}CF_3$;
$R^8$, $R^9$ and $R^{10}$ are each independently selected from hydrogen, $C_{1-6}$ alkyl, $C_{3-6}$ cycloalkyl, $(CH_2)_{2-4}OR^{15}$ or $(CH_2)_{0-2}CF_3$;
$R^{13}$ is selected from hydrogen, $C_{1-6}$ alkyl, $C_{3-6}$ cycloalkyl, $(CH_2)_{2-4}OR^{15}$, $(CH_2)_{0-2}CF_3$, or unsubstituted, mono-, or di-substituted phenyl wherein the substitutents on the phenyl are independently selected from halogen, $CF_3$, cyano, $CO_2R^{16}$, $OR^{15}$ or $C_{1-4}$ alkyl;
$R^{15}$ is selected from hydrogen, $C_{1-6}$ alkyl, $C_{3-6}$ cycloalkyl or $(CH_2)_{0-2}CF_3$;
$R^{16}$ is selected from hydrogen, $C_{1-6}$ alkyl, $C_{3-6}$ cycloalkyl or $(CH_2)_{1-2}CF_3$;
$R^{19}$ is selected from hydrogen, $C_{1-6}$ alkyl, $C_{3-6}$ cycloalkyl, $(CH_2)_{0-4}OR^{15}$ or $(CH_2)_{0-2}CF_3$;
each X is independently selected from halogen or $C_{1-4}$ alkyl, p is an integer from zero to two;
q is an integer from zero to three;
and all other variables are as defined above;
and the pharmaceutically acceptable salts thereof
In a subclass of the inention is the compound of the formula

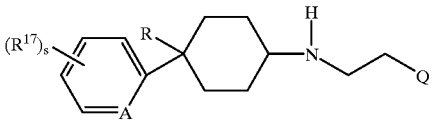

wherein Q is

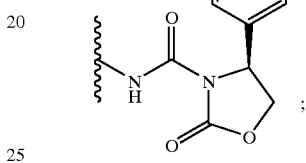

A is C—$R^{17}$ or N;
R is selected from hydrogen, cyano, hydroxy, $CO_2R^{15}$, $CON(R^{16})_2$, $SO_2R^{15}$ or $SO_2N(R^{16})_2$;
each $R^{17}$ is independently selected from hydrogen, halogen, $CO_2R^{16}$, cyano, nitro, $CON(R^{16})_2$, $SO_2R^{15}$, $SO_2N(R^{16})_2$ or $OR^{15}$;
each X is independently selected from flourine or methyl;
s is an integer from zero to two;
and all other variables are as defined above;
and the pharmaceutically acceptable salts thereof.
Illustrative of the invention is the compound selected from
(4-cyano-4-phenyl-cyclohexyl)-[3-(2,2-di-p-tolyl-acetylamino)-propyl]-methyl-ammonium chloride;
(4-cyano-4-phenyl-cyclohexyl)-methyl-[4-(1,1,3-trioxo-1,3-dihydro-1l6-benzo[d]isothiazol-2yl)-butyl]-ammonium chloride;
(4-cyano-4-phenyl-cyclohexyl)-methyl-[3-(1,1,3-trioxo-1,3-dihydro-1l6-benzo[d]isothiazol-2-yl)-propyl]-ammonium chloride;
(+)-2-Oxo-4-(3,4,5-trifluorophenyl)-oxazolidine-3-carboxylic acid [2-(4-cyano-4-phenyl-cyclohexylamino)-ethyl]amide;
(+)-2-Oxo-4-(3,4-difluorophenyl)-oxazolidine-3-carboxylic acid [2-(4-phenyl-4-methoxycarbonyl-cyclohexylamino)-ethyl]amide;
(+)-cis-2-Oxo-4-(3,4-difluorophenyl)-oxazolidine-3-carboxylic acid [2-(4-Cyano-4-(2-ethoxyphenyl)-cyclohexylamino)-ethyl]amide;
[4-cyano-4-(2-methoxy-phenyl)-cyclohexyl]-(2-{[4-(3,4-difluoro-phenyl)-2-oxo-oxazolidine-3-carbonyl]-amino}-ethyl)-ammonium chloride;
[4-cyano-4-(2-fluoro-phenyl)-cyclohexyl]-(2-{[4-(3,4-difluoro-phenyl)-2-oxo-oxazolidine-3-carbonyl]-amino}-ethyl)-ammonium chloride;
4-(3,4-difluoro-phenyl)-2-oxo-oxazolidine-3-carboxylic acid {2-[4-cyano-4-(2-trifluoromethoxy-phenyl)-cyclohexylamino]-ethyl}-amide;
4-(3,4-difluoro-phenyl)-2-oxo-oxazolidine-3-carboxylic acid {2-[4-cyano-4-(2-trifluoromethoxy-phenyl)-cyclohexylamino]-ethyl}-amide;

4-(3,4-difluoro-phenyl)-2-oxo-oxazolidine-3-carboxylic acid {2-[4-cyano-4-(2-trifluoromethyl-phenyl)-cyclohexylamino]-ethyl}-amide;

4-(3,4-difluoro-phenyl)-2-oxo-oxazolidine-3-carboxylic acid {2-[4-cyano-4-(2-trifluoromethyl-phenyl)-cyclohexylamino]-ethyl}-amide;

(2-{[4-(3,4-difluoro-phenyl)-2-oxo-oxazolidine-3-carbonyl]-amino}-ethyl)-(4-methanesulfonyl-4-phenyl-cyclohexyl)-ammonium chloride; or (2-{[4-(3,4-difluoro-phenyl)-2-oxo-oxazolidine-3-carbonyl]-amino}-ethyl)-(4-methanesulfonyl-4-phenyl-cyclohexyl)-ammonium chloride and the pharmaceutically acceptable salts thereof.

An illustration of the invention is a pharmaceutical composition comprising a therapeutically effective amount of any of the compounds described above and a pharmaceutically acceptable carrier. An example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Exemplifying the invention is the composition further comprising a therapeutically effective amount of a testosterone 5-alpha reductase inhibitor. Preferably, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor) or a dual type 1 and type 2 testosterone 5-alpha reductase inhibitor. More preferably, the testosterone 5-alpha reductase inhibitor is a type 2 testosterone 5-alpha reductase inhibitor. Most preferably, the testosterone 5-alpha reductase inhibitor is finasteride.

More specifically illustrating the invention is a method of treating benign prostatic hyperplasia in a subject in need thereof which comprises administering to the subject a therapeutically effective amount of any of the compounds (or any of the compositions) described above.

Further exemplifying the invention is the method of treating BPH wherein the compound (or composition) additionally does not cause a fall in blood pressure at dosages effective to alleviate BPH.

Another example of the invention is the method of treating benign prostatic hyperplasia wherein the compound is administered in combination with a testosterone 5-alpha reductase inhibitor. Preferably, the testosterone 5-alpha reductase inhibitor is finasteride.

Further illustrating the invention is a method of inhibiting contraction of prostate tissue or relaxing lower urinary tract tissue in a subject in need thereof which comprises administering to the subject a therapeutically effective amount of any of the compounds (or any of the compositions) described above.

More specifically exemplifying the invention is the method of inhibiting contraction of prostate tissue or relaxing lower urinary tract tissue wherein the compound (or composition) additionally does not cause a fall in blood pressures at dosages effective to inhibit contraction of prostate tissue.

More particularly illustrating the invention is the method of inhibiting contraction of prostate tissue or relaxing lower urinary tract tissue wherein the compound (or composition) is administered in combination with a testosterone 5-alpha reductase inhibitor; preferably, the testosterone 5-alpha reductase inhibitor is finasteride.

More particularly exemplifying the invention is a method of treating a disease which is susceptible to treatment by antagonism of the alpha 1a receptor which comprises administering to a subject in need thereof an amount of any of the compounds described above effective to treat the disease. Diseases which are susceptible to treatment by antagonism of the alpha 1a receptor include, but are not limited to, BPH, high intraocular pressure, high cholesterol, impotency, sympathetically mediated pain, migraine (see, K. A. Vatz, *Headache* 1997:37: 107–108) and cardiac arrhythmia.

An additional illustration of the invention is the use of any of the compounds described above in the preparation of a medicament for: a) the treatment of benign prostatic hyperplasia; b) relaxing lower urinary tract tissue; or c) inhibiting contraction of prostate tissue; in a subject in need thereof.

An additional example of the invention is the use of any of the alpha 1a antagonist compounds described above and a 5-alpha reductase inhibitor for the manufacture of a medicament for: a) treating benign prostatic hyperplasia; b) relaxing lower urinary tract tissue; or c) inhibiting contraction of prostate tissue which comprises an effective amount of the alpha 1a antagonist compound and an effective amount of 5-alpha reductase inhibitor, together or separately.

DETAILED DESCRIPTION OF THE INVENTION

Representative compounds of the present invention exhibit high selectivity for the human alpha 1a adrenergic receptor. One implication of this selectivity is that these compounds display selectivity for lowering intraurethral pressure without substantially affecting diastolic blood pressure.

Representative compounds of this invention display submicromolar affinity for the human alpha 1a adrenergic receptor subtype while displaying at least ten-fold lower affinity for the human alpha 1d and alpha 1b adrenergic receptor subtypes, and many other G-protein coupled human receptors. Particular representative compounds of this invention exhibit nanomolar and subnanomolar affinity for the human alpha 1a adrenergic receptor subtype while displaying at least 30 fold lower affinity for the human alpha 1d and alpha 1b adrenergic receptor subtypes, and many other G-protein coupled human receptors (e.g., serotonin, dopamine, alpha 2 adrenergic, beta adrenergic or muscarinic receptors).

These compounds are administered in dosages effective to antagonize the alpha 1a receptor where such treatment is needed, as in BPH. For use in medicine, the salts of the compounds of this invention refer to non-toxic "pharmaceutically acceptable salts." Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate.

Compounds of this invention are used to reduce the acute symptoms of BPH. Thus, compounds of this invention may be used alone or in conjunction with a more long-term anti-BPH therapeutics, such as testosterone 5α-reductase inhibitors, including PROSCAR® (finasteride). Aside from their utility as anti-BPH agents, these compounds may be used to induce highly tissue-specific, localized alpha 1a adrenergic receptor blockade whenever this is desired. Effects of this blockade include reduction of intra-ocular pressure, control of cardiac arrhythmias, and possibly a host of alpha 1a receptor mediated central nervous system events.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Where the compounds according to the invention have at least one chiral center, they may accordingly exist as enantiomers. Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also encompassed within the scope of this invention.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "aryl" as used herein, except where otherwise specifically defined, refers to unsubstituted, mono- or poly-substituted aromatic groups such as phenyl or naphthyl.

The term "cycloalkyl" shall mean cyclic rings of alkanes of three to eight total carbon atoms (i.e., cyclopropyl, cyclobutyl, cyclopentyl, cyclohexyl, cycloheptyl or cyclooctyl).

Whenever the term "alkyl" or "aryl" or either of their prefix roots appear in a name of a substituent (e.g., aralkoxyaryloxy) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The term "halogen" shall include iodine, bromine, chlorine and fluorine.

The term "substituted" shall be deemed to include multiple degrees of substitution by a named substitutent. The term "poly-substituted" as used herein shall include di-, tri-, tetra- and penta-substitution by a named substituent.

It is intended that the definition of any substituent or variable (e.g., X, $R^{16}$, $R^{18}$) at a particular location in a molecule be independent of its definitions elsewhere in that molecule. Thus, —understood $N(R^{16})_2$ represents —$NH_2$, —$NHCH_3$, —$NHC_2H_5$, —$N(CH_3)C_2H_5$, etc. It is understood that substituents and substitution patterns on the compounds of the instant invention can be selected by one of ordinary skill in the art to provide compounds that are chemically stable and that can be readily synthesized by techniques known in the art as well as those methods set forth below.

Where multiple substituent moieties are disclosed or claimed, the substituted compound can be independently substituted by one or more of the disclosed or claimed substituent moieties, singly or plurally.

The term "Z is hydrogen," when refering to the "Q" group

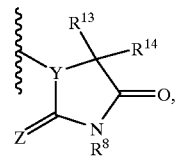

refers to the moiety

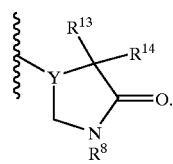

The term heterocycle or heterocyclic ring, as used herein, represents an unsubstituted or substituted stable 5- to 7-membered monocyclic ring system which may be saturated or unsaturated, and which consists of carbon atoms and from one to three heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. Morpholino is the same as morpholinyl.

The term "(S)-oxa" as used herein, refers to an oxazolidinone group of the formula

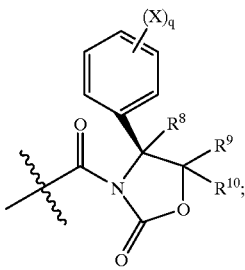

for example,

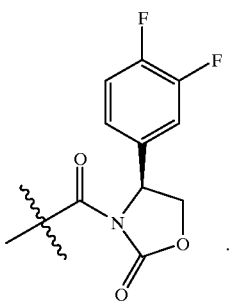

The term "activated (S)-oxa" as used herein, refers to an N-(activated)carbamate of the desired oxazolidinone where the activating group is, for example, a p-nitrophenyloxy group. A specific example of an activated (S)-oxa group is 4-(3,4-difluorophenyl)-2-oxo-oxazolidine-3-carboxylic acid 4-nitrophenyl ester (i.e., compound 2).

The term "selective alpha 1a adrenergic receptor antagonist," as used herein, refers to an alpha 1a antagonist compound which is at least ten fold selective for the human alpha 1a adrenergic receptor as compared to the human alpha 1b, alpha 1d, alpha 2a, alpha 2b and alpha 2c adrenergic receptors.

The term "lower urinary tract tissue," as used herein, refers to and includes, but is not limited to, prostatic smooth muscle, the prostatic capsule, the urethra and the bladder neck.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, the term "composition" is intended to encompass a product comprising the specified ingredients in the specified amounts, as well as any product which results, directly or indirectly, from combination of the specified ingredients in the specified amounts.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

The specificity of binding of compounds showing affinity for the alpha 1a receptor is shown by comparing affinity to membranes obtained from tranfected cell lines that express the alpha 1a receptor and membranes from cell lines or tissues known to express other types of alpha (e.g., alpha 1d, alpha 1b) or beta adrenergic receptors. Expression of the cloned human alpha 1d, alpha 1b, and alpha 1a receptors and comparison of their binding properties with known selective antagonists provides a rational way for selection of compounds and discovery of new compounds with predictable pharmacological activities. Antagonism by these compounds of the human alpha 1a adrenergic receptor subtype may be functionally demonstrated in anesthetized animals. These compounds may be used to increase urine flow without exhibiting hypotensive effects.

The ability of compounds of the present invention to specifically bind to the alpha 1a receptor makes them useful for the treatment of BPH. The specificity of binding of compounds showing affinity for the alpha 1a receptor is compared against the binding affinities to other types of alpha or beta adrenergic receptors. The human alpha adrenergic receptor of the 1a subtype was recently identified, cloned and expressed as described in PCT International Application Publication Nos. WO94/08040, published Apr. 14, 1994 and WO 94/21660, published Sep. 29, 1994. The cloned human alpha 1a receptor, when expressed in mammalian cell lines, is used to discover ligands that bind to the receptor and alter its function. Expression of the cloned human alpha 1d, alpha 1b, and alpha 1a receptors and comparison of their binding properties with known selective antagonists provides a rational way for selection of compounds and discovery of new compounds with predictable pharmacological activities.

Compounds of this invention exhibiting human alpha 1a adrenergic receptor antagonism may further be defined by counterscreening. This is accomplished according to methods known in the art using other receptors responsible for mediating diverse biological functions. [See e.g., PCT International Application Publication No. WO94/10989, published May 26, 1994; U.S. Pat. No. 5,403,847, issued Apr. 4, 1995]. Compounds which are both selective amongst the various human alpha1 adrenergic receptor subtypes and which have low affinity for other receptors, such as the alpha2 adrenergic receptors, the β-adrenergic receptors, the muscarinic receptors, the serotonin receptors, and others are particularly preferred. The absence of these non-specific activities may be confirmed by using cloned and expressed receptors in an analogous fashion to the method disclosed herein for identifying compounds which have high affinity for the various human alpha1 adrenergic receptors. Furthermore, functional biological tests are used to confirm the effects of identified compounds as alpha 1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha 1a adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1a antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyl-eneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Compounds of this invention may be administered in any of the foregoing compositions and according to dosage regimens established in the art whenever specific blockade of the human alpha 1a adrenergic receptor is required.

The daily dosage of the products may be varied over a wide range from 0.01 to 1,000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 20 mg/kg of body weight per day. Preferably, the range is from about 0.001 to 10 mg/kg of body weight per day, and especially from about 0.001 mg/kg to 7 mg/kg of body weight per day. The compounds may be administered on a regimen of 1 to 4 times per day.

Compounds of this patent disclosure may be used alone at appropriate dosages defined by routine testing in order to obtain optimal antagonism of the human alpha 1a adrenergic receptor while minimizing any potential toxicity. In addition, co-administration or sequential administration of other agents which alleviate the effects of BPH is desirable. Thus, in one embodiment, this includes administration of compounds of this invention and a human testosterone 5α-reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. Nos. 4,377,584 and 4,760,071, for example). In addition to PROSCAR®, which is principally active in prostatic tissue due to its selectivity for human 5α-reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5α-reductase inhibitors have been described in WO93/23420, EP 0572166; WO 93/23050; WO93/23038,; WO93/23048; WO93/23041; WO93/23040; WO93/23039; WO93/23376; WO93/123419, EP 0572165; WO93/23051.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one preferred embodiment of the present invention, a method of treating BPH is provided which comprises administering to a subject in need of treatment any of the compounds of the present invention in combination with finasteride effective to treat BPH. The dosage of finasteride administered to the subject is about 0.01 mg per subject per day to about 50 mg per subject per day in combination with an alpha 1a antagonist. Preferably, the dosage of finasteride in the combination is about 0.2 mg per subject per day to about 10 mg per subject per day, more preferably, about 1 to about 7 mg per subject to day, most preferably, about 5 mg per subject per day.

For the treatment of benign prostatic hyperplasia, compounds of this invention exhibiting alpha 1a adrenergic receptor blockade can be combined with a therapeutically effective amount of a 5α-reductase 2 inhibitor, such as finasteride, in addition to a 5α-reductase 1 inhibitor, such as 4,7β-dimethyl-4-aza-5α-cholestan-3-one, in a single oral, systemic, or parenteral pharmaceutical dosage formulation. Alternatively, a combined therapy can be employed wherein the alpha 1a adrenergic receptor antagonist and the 5α-reductase 1 or 2 inhibitor are administered in separate oral, systemic, or parenteral dosage formulations. See, e.g., U.S. Pat. No.'s 4,377,584 and 4,760,071 which describe dosages and formulations for 5α-reductase inhibitors.

Abbreviations used in the instant specification, particularly the Schemes and Examples, are as follows:

AcOH or HOAc=acetic acid
BCE=bromochloroethane
Boc or BOC=t-butyloxycarbonyl
Boc$_2$O=di-tert-butyl dicarbonate
BOPCl=bis(2-oxo-3-oxazolidinyl)phosphinic chloride
Cbz-Cl=benzyloxycarbonyl chloride
DEAD=diethylazodicarboxylate
DMF=N,N-dimethylformamide
DMSO=dimethylsulfoxide
D-S=Dean Stark
EDCI=1-(3-dimethylaminopropyl)-3-ethylcarbodiimide hydrochloride
Et=ethyl
Et$_3$N=triethylamine
EtOAc=ethyl acetate
EtOH=ethanol FABLRMS=fast atom bombardment low resolution mass spectroscopy HPLC=high performance liquid chromatography HOBt=1-hydroxy benzotriazole hydrate i-PrOH=2-propanol i-Pr$_2$NEt=diisopropylethylamine LAH=lithium aluminum hydride mCPBA=meta-chloroperbenzoic acid Me=methyl MeOH=methanol NMR=nuclear magnetic resonance PCTLC=preparative centrifugal thin layer chromatography PEI=polyethylenimine Ph=phenyl RT=retention time tBuOH=tert-butanol TEBAC=benzyltriethylammonium chloride TFA=trifluoroacetic acid THF=tetrahydrofuran TLC=thin layer chromatography TMS=trimethylsilyl Tos$_2$O=p-toluenesulfonicanhydride Triton B=N-benzyltrimethylammonium hydroxide The compounds of the present invention can be prepared readily according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Unless otherwise indicated, all variables are as defined above.

The general synthetic approach to analogs claimed within this application is outlined in Scheme 1. Starting from ketone A, reductive amination with a mono blocked diamino species provides an intermediate which can be alkylated on the newly generated secondary amine. Deprotection of the terminal blocked amine and acylation, alkylation, etc. provides the desired analogs.

For example, a substituted benzyl nitrile, sulphone, etc. can be added to methyl acrylate, submitted to Dieckman cyclization, hydrolyzed and decarboxylated providing appropriately substituted ketones A. Scheme 2 depicts a more specific series of compounds derived from Michael addition of substituted benzyl nitriles to methyl acrylate, Dieckman cyclization, providing the β-keto ester which can be either: (a) submitted to a reductive amination and carried on to final products, (b) enolized and alkylated then reductively aminated, deprotected and further manipulated providing further substituted analogs; or (c) hydrolyzed and decarboxylated and run through the above described conditions producing the desired antagonists.

Another strategy for the synthesis of some geminally disubstituted cyclic ketones, in particular, 4,4-disubstituted cyclohexanones was accomplished as outlined in Scheme 3 starting from benzophenone derivatives and substituted methyl vinyl ketones which under basic conditions lead to the 4,4-diaryl cyclohex-2-en-1-ones in good yield. Subsequent hydrogenation, reductive amination and deprotection provided the appropriate acylation/alkylation precursors.

Some examples were prepared by first assembling the appropriately substituted amino bearing cycloalkyl, then allylating the amino moiety. This approach is described in Scheme 4. Starting with a cycloalkanone, for instance, 4-cyano 4-phenyl piperidone, reductive amination with ammonium acetate and sodium cyanoborohydride provides both the cis and trans 1-amino cyclohexanes. The ratio of these isomers is modulated by the choice of an appropriate reducing reagent. The incipient amino group could be protected, alkylated, deprotected and alkylated again providing more funtionalized analogs.

Antagonists with alkyl (straight or branched chain) can be assembled by reductive amination of the prerequisite aminoalcohol and a cycloketone, for example, 4-cyano 4-phenylcyclohexanone, Scheme 5. Boc protection of the amine, followed by tosylation of the hydroxy and displacement by the lithium or sodium salt of the desired Q group completes the synthesis of the targeted antagonists.

The selective acylation of the primary amines was accomplished by treatment with nearly equimolar quantities of the activated termini species (i.e., the "Q" groups). The activated termini species comprising the "Q" groups are readily prepared by one of ordinary skill in the art. For example, oxazolidinones are prepared and activated in general by published and well developed chemistry, in particular, of Evans. [Evans, D. A. ; Nelson, J. V. ; Taber, T. R. Top. Stereochem. 13, 1 (1982)] The starting materials, in general, are natural and unnatural amino acids. For instance, some of the preferred compounds are prepared from substituted phenyl glycine derivatives, which after reduction of the carboxylate and a phosgene equivalent mediated cyclization provides the substituted oxazolidinone ring system. Deprotonation with n-butyl lithium and addition to a THF solution of p-nitrophenylchloroformate produces the stable, isolable "activated" oxazolidinone (oxa).

Hydantoins and cycloimide were prepared in two chemical steps from ketones as outlined in the literature. More specifically, hydantoins were prepared according to known methodology, e.g., J. J. Edmunds et al., *J. Med. Chem.* 1995, 38, pp. 3759–3771; J. H. Poupart et al., *J. Chem. Res.* 1979, pp. 174–175. Saccharins were prepared according to known methods, e.g., page 40 and Examples 21 and 22 of PCT International Application Publication No. WO96/25934, published Aug. 29, 1996.

The oxazolidinones were synthesized independently in racemic form, and then separated utilizing preparative chiral HPLC. Their optical rotations were recorded. Then they were activated and reacted with prerequisite amines. From the receptor binding studies, a preferred isomer was identified, the (+) rotational isomer. The absolute configurations were determined to be (S) for the oxazolidinones by correlating their optical rotations with x-ray crystal structures obtained of fragments involved in the production of the antagonists.

SCHEME 1: Synthesis of Cycloalkylaminoethylamines
In general:
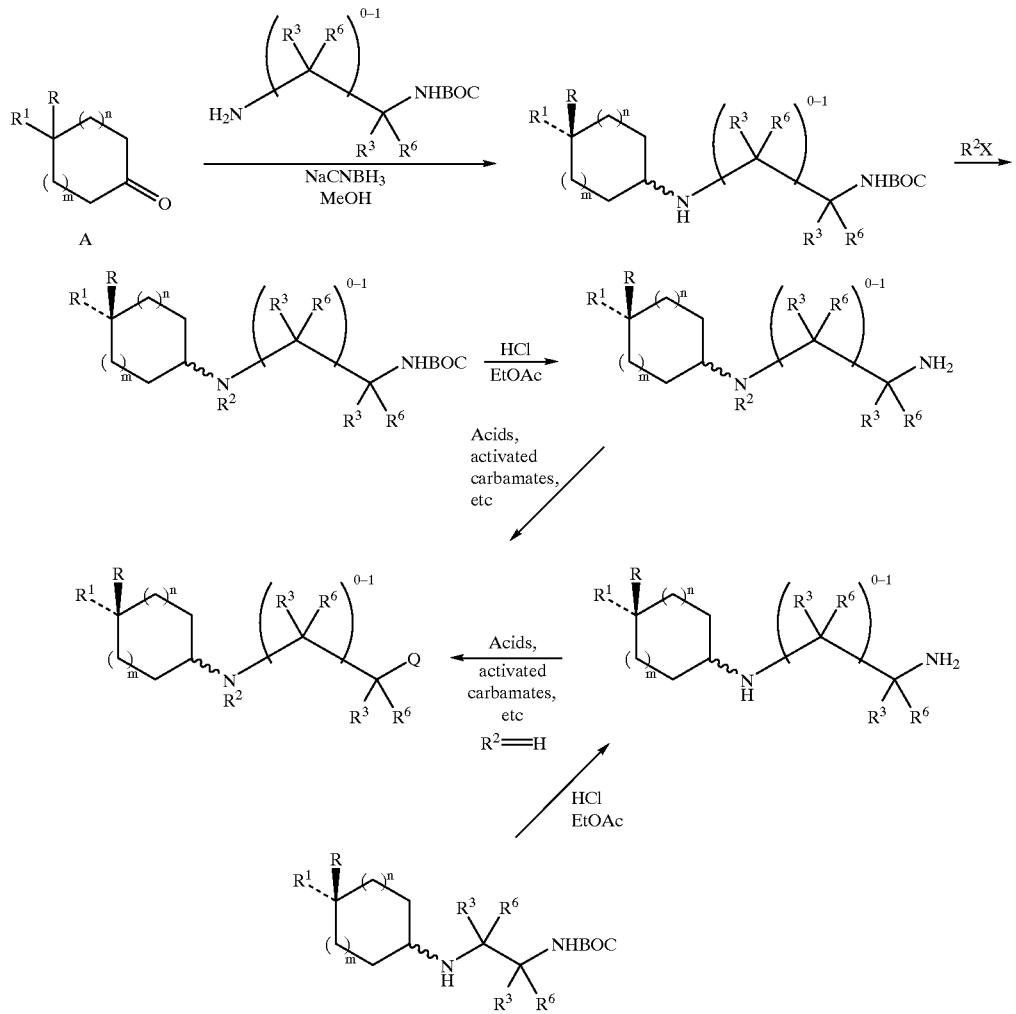
For example,
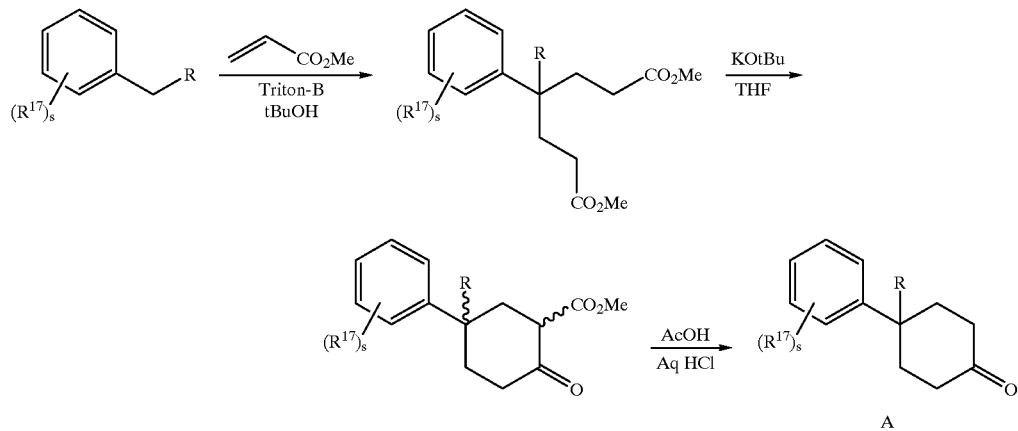

SCHEME 4
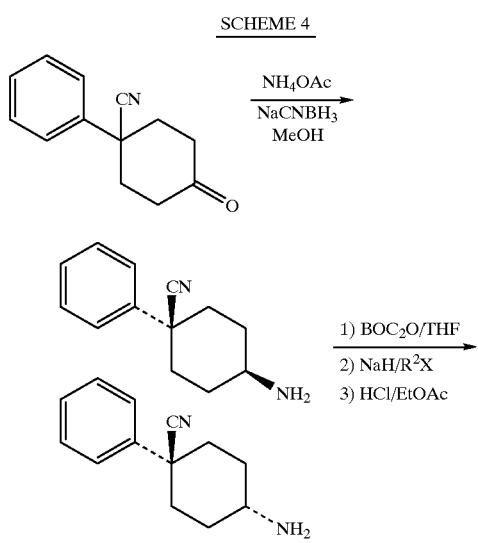
SCHEME 5
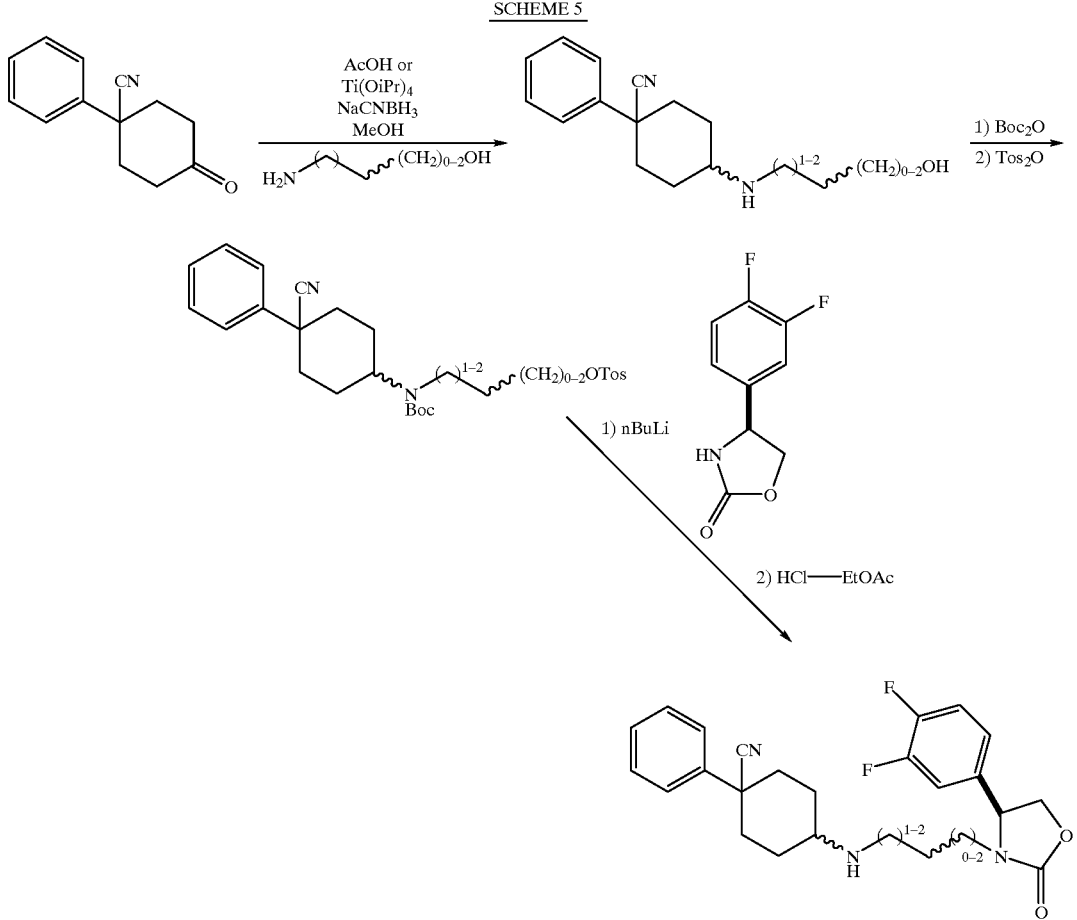

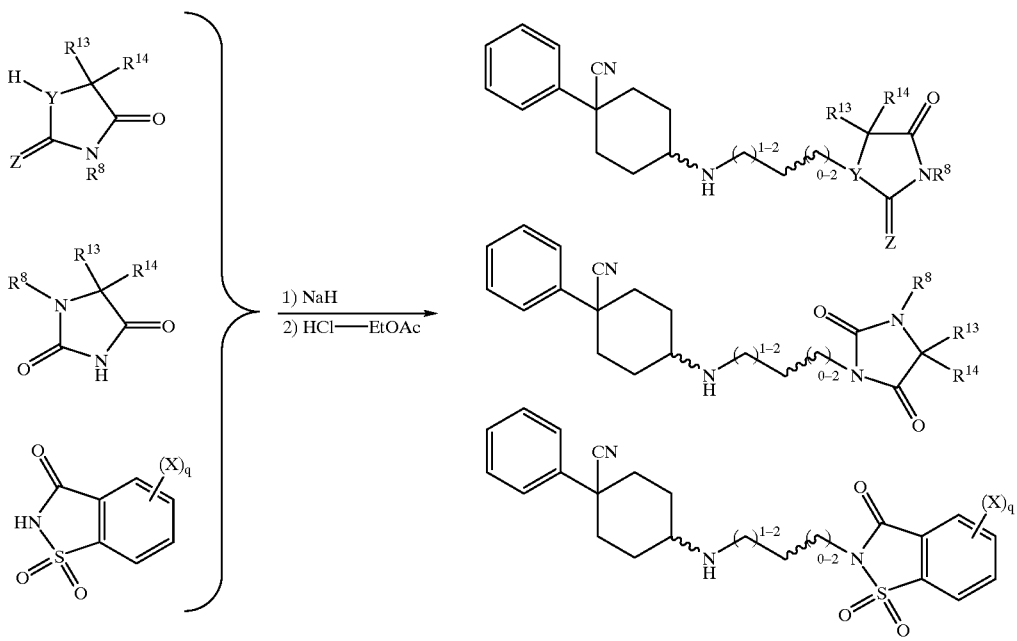

The following examples are provided to further define the invention without, however, limiting the invention to the particulars of these examples.

EXAMPLE 1

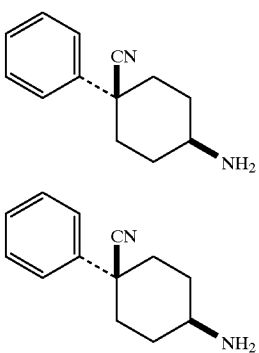

cis 1-amino 4-cyano 4-phenylcyclohexane and trans 1-amino 4-cyano 4-phenylcyclohexane A solution of 4-cyano 4-phenylcyclohexanone (6.0 g, 30 mmol), 8.0 g 4 Å molecular sieves and ammonium acetate (23.2 g, 300 mmol) in methanol (200 mL) (1.5 h premixed) was treated with sodium cyanoborohydride (1.9 g, 30 mmol) at room temperature. The resulting mixture was stirred at room temperature (60 min), then concentrated in vacuo and the residue dissolved in EtOAc and sodium bicarbonate solution. The aqueous layer was extracted with one additional portion of EtOAc, the combined organic extracts were washed with brine, dried over $Na_2SO_4$, and concentrated under reduced pressure. PCTLC ($SiO_2$, 6 mm, 0–10% MeOH—$CHCl_3$) provided the two title compounds. The cis (more polar isomer) and trans isomer (less polar isomer). cis isomer: $^1$H NMR ($CDCl_3$, 300 MHz) 7.49 (br d, 2 H, ArH), 7.39 (br t, 2 H, ArH), 7.33 (br m, 1 H, ArH), 2.76 (br m, 1 H, $CHNH_2$), 2.21 (br d, 2 H), 2.03 (br dd, 2 H), 1.88 (br ddd, 2 H), 1.73 (br ddd, 2 H)

Anal. Calcd for $C_{13}H_{16}N_2$: C=77.96, H=8.05, N=13.99. Found: C=78.00, H=7.94, N=13.82.

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=5.87 min; focus=215 nm; 97.4% pure. trans isomer: $^1$H NMR ($CDCl_3$, 300 MHz) 7.53 (br m, 2 H, ArH), 7.38 (br m, 2 H, ArH), 7.34 (br m, 1 H, ArH), 3.37 (dd, 1 H, $CHNH_2$), 2.36 (ddd, 2 H), 2.08 (br ddd, 2 H), 1.91 (br dd, 2 H), 1.67 (br dd, 2 H)

Anal. Calcd for $C_{13}H_{16}N_2 \cdot 0.15 H_2O$ C=77.96, H=8.05, N=13.99. Found: C=76.85, H=7.87, N=13.82.

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=5.68 min; focus=215 nm; 98.4% pure.

EXAMPLE 2

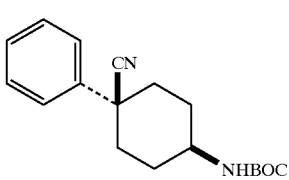

cis 1-N-(1,1-dimethylethoxycarbonyl)amino-4-cyano 4-phenylcyclohexane

A solution of the amine (3.0 g, 15 mmol) and $BOC_2O$ (3.3 g, 15 mmol) in THF (40 mL) was mixed at room temperature for 1 h. The resulting mixture was concentrated in vacuo to afford the title compound.

cis isomer: ¹H NMR (CDCl₃, 300 MHz) 7.47 (br m, 2 H, ArH), 7.40 (br m, 2 H, ArH), 7.35 (br m, 1 H, ArH), 4.52 (br d, 1 H, NHC=O), 3.52 (br s, 1 H, CHNH), 2.40 (br m, 4 H), 1.92 (br ddd, 2 H), 1.71 (br ddd, 2 H), 1.46 (br s, 9 H)

EXAMPLE 3

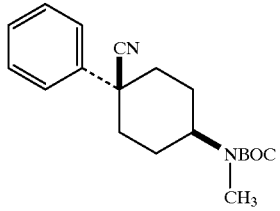

cis 1-N-[(1,1-dimethylethoxycarbonyl)methyl] amino-4-cyano 4-phenylcyclohexane

A solution of the BOC carbamate (2.0 g, 15 mmol) in DMF (10 mL) was treated with NaH (290 mg, 7.33 mmol) and iodomethane at 0° C. for 4 h. The resulting mixture was diluted with water (50 mL), extracted with EtOAc (3×50 mL), washed with brine (1×75 mL), dried (Na₂SO₄), filtered and concentrated in vacuo. PCTLC 0–50% EtOAc/hexane afforded the title compound.

cis isomer: ¹H NMR (CDCl₃, 300 MHz) 7.48 (br m, 2 H, ArH), 7.43 (br m, 2 H, ArH), 7.34 (br m, 1 H, ArH), 4.16 (br d, 1 H, CHNH), 2.83 (br s, 3 H, NCH₃), 2.25 (br d, 2 H), 1.80–2.10 (br m, 6 H), 1.49 (br s, 9 H)

EXAMPLE 4

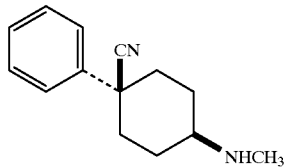

cis 1-N-methylamino-4-cyano 4-phenylcyclohexane

A solution of the BOC carbamate (1.5 g, 4.8 mmol) was treated saturated HCl-EtOAc at 0° C. The resulting mixture was allowed to warm to room temperature (1 h) then concentrated in vacuo affording the title compound.

Anal. Calcd for $C_{14}H_{18}N_2 \cdot HCl$: C=67.05, H=7.64, N=11.17. Found: C=66.92, H=7.51, N=11.20.

HPLC (Vydac; C18; diameter=4.6 mm; length=150 mm; gradient=H₂O [0.1% H₃PO₄]—CH₃CN, 95%–5%, 5%–95%, over 16 minutes, 2 ml/min flow rate) RT=5.91 min; focus=215 nm; 100% pure.

EXAMPLE 5

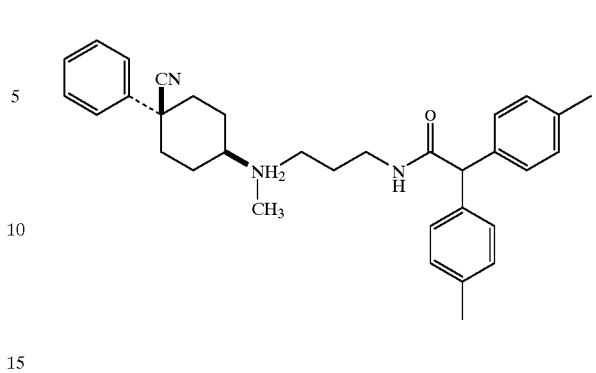

(4-cyano-4-phenyl-cyclohexyl)-[3-(2,2-di-p-tolyl-acetylamino)-propyl]-methyl-ammonium chloride A solution of the amine (75.0 mg, 0.35 mmol), Br(CH2)₃NHCOCH(p-tolyl)₂ (140 mg, 0.385 mmol) and iPr₂NEt (54.3 mg, 0.42 mmol) was stirred in DMF (1 mL) at room temperature (12 h). The solvent was removed in vacuo and submitted to PCTLC (SiO₂, 2 mm, CHCl₃-90:10:1 CHCl₃:CH₃OH:NH₄OH providing the title compound which was converted to the hydrochloride salt by treatment with HCl-EtOAc.

cis isomer: ¹H NMR (DMSO-d₆, 400 MHz) 8.44 (br t, 1 H, NH), 7.53 (br d, 2 H, ArH), 7.47 (br t, 2 H, ArH), 7.39 (br m, 1 H, ArH), 7.18 (br dd, 4 H, ArH), 7.1 (br d, 4 H, ArH), 4.83 (br s, 1 H, CHC=O), 3.19 (br m, 2 H), 3.04 (br m, 2 H), 2.50 (br s, 7 H, CHNCH₃ and ArCH₃), 2.24 (br s, 3 H, NCH₃), 2.21 (br m, 2 H), 2.10 (br d, 2 H), 1.95 (br m, 2 H), 1.82 (br m, 2 H), 1.72 (br m, 2H)

Anal. Calcd for $C_{33}H_{39}N_3O \cdot 2H_2O$: C=70.00, H=7.83, N=7.42. Found: C=69.92, H=7.51, N=7.08.

HPLC (Vydac; C18; diameter=4.6 mm; length=150 mm; gradient=H₂O [0.1% H₃PO₄]—CH₃CN, 95%–5%, 5%–95%, over 16 minutes, 2 ml/min flow rate) RT=10.66 min; focus=215 nm; 96.7% pure.

EXAMPLE 6

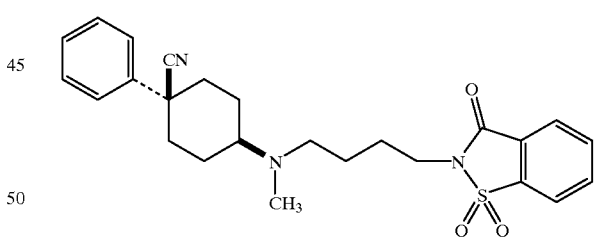

(4-cyano-4-phenyl-cyclohexyl)-methyl-[4-(1,1,3-trioxo-1,3-dihydro-1l6-benzo[d]isothiazol-2-yl)-butyl]-ammonium chloride A solution of the amine (99.6 mg, 0.465 mmol), Br(CH2)₄-N(saccharin) (178 mg, 0.558 mmol) and iPr₂NEt (72 mg, 0.558 mmol) was stirred in DMF (1 mL) at room temperature (12 h). The solvent was removed in vacuo and submitted to PCTLC (SiO₂, 2 mm, CHCl₃-95:5 CHCl₃:CH₃OH providing the title compound (193.2 mg, 210 mg theoretical, 92%) which was converted to the hydrochloride salt by treatment with HCl-EtOAc.

cis isomer: ¹H NMR (CDCl₃, 300 MHz) 8.07 (dd, 1 H, ArH), 7.90 (br dd, 1 H, ArH), 7.87 (br m, 2 H, ArH), 7.48

(br d, 2 H, ArH), 7.28–7.42 (br m, 3 H, ArH), 3.83 (t, 2 H, J=7.5 Hz), 2.56 (br m, 3 H), 2.32 (br 2, 3 H, NCH$_3$), 2.24 (br d, 2 H), 1.80–2.00 (br m, 8 H), 1.60 (br m, 2 H).

Anal. Calcd for C$_{25}$H$_{29}$N$_3$O$_3$S.1 HCl & 0.25 H$_2$O: C=60.96, H=6.24, N=8.53. Found: C=60.97, H=6.08, N=8.57.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=8.53 min; focus=215 nm; 100% pure.

EXAMPLE 7

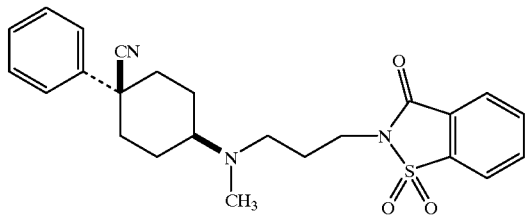

(4-cyano-4-phenyl-cyclohexyl)-methyl-[3-(1,1,3-trioxo-1,3-dihydro-1l6-benzo[d]isothiazol-2-yl)-propyl]-ammonium chloride A solution of the amine (80.0 mg, 0.3733 mmol), Br(CH2)$_3$-N(saccharin) (119.2 mg, 0.392 mmol) and iPr$_2$NEt (53 mg, 0.411 mmol) was stirred in DMF (1 mL) at room temperature (12 h). The solvent was removed in vacuo and submitted to PCTLC (SiO$_2$, 2 mm, CHCl$_3$-95:5 CHCl$_3$:CH$_3$OH providing the title compound.

cis isomer: $^1$H NMR (CDCl$_3$, 300 MHz) 8.04 (dd, 1 H, ArH), 7.90 (br dd, 1 H, ArH), 7.87 (br m, 2 H, ArH), 7.49 (br d, 2 H, ArH), 7.28–7.42 (br m, 3 H, ArH), 3.83 (t, 2 H, J=7.5 Hz), 2.64 (br t, 2 H), 2.56 (br m, 1 H), 2.32 (br 2, 3 H, NCH$_3$), 2.24 (br d, 2 H), 1.80–2.00 (br m, 8 H).

Anal. Calcd for C$_{24}$H$_{27}$N$_3$O$_3$S. 0.25 CHCl$_3$: C=65.12, H=6.15, N=9.47. Found: C=65.19, H=5.76, N =9.34.

EXAMPLE 8

A

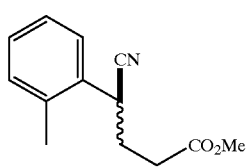

B

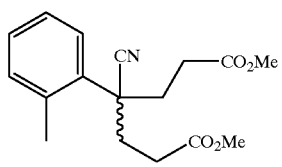

A: 5-nitrilo-4-o-tolyl-pentanoic acid methyl ester

B: 4-cyano-4-o-tolyl-heptanedioic acid dimethyl ester

A solution of 2-methylbenzyl nitrile (25.0 g), methyl acrylate (75 mL) and Triton-B (40 µmL) in t-butanol (90 mL) was refluxed (12 h). The solvent was removed in vacuo and submitted to SGC (SiO$_2$, 10 cm×30 cm, 0–15% EtOAc-hexane) affording the mono addition product and the desired bis addition compound (5).

A: $^1$H NMR (CDCl$_3$, 300 MHz) 7.42 (m, 1 H, ArH), 7.20 (m, 3 H, ArH), 4.34 (dd, 1 H, CHCN), 3.69 (s, 3 H, OMe), 2.57 (m, 2 H), 2.37 (s, 3 H, Me), 2.16 (m, 2 H).

B: $^1$H NMR (CDCl$_3$, 300 MHz) 7.42 (m, 1 H, ArH), 7.20 (m, 3 H, ArH), 3.62 (s, 6 H, OMe), 2.57 (m, 4 H), 2.54 (s, 3 H, Me), 2.31 (m, 2 H).

EXAMPLE 9

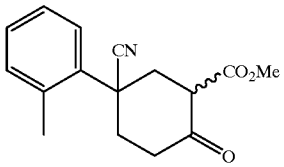

5-cyano-2-oxo-5-o-tolyl-cyclohexanecarboxylic acid methyl ester

A solution of the diester (9.38 g, 29.4 mmol) in THF (200 mL) was treated with KOt-Bu (6.6 g, 58.74 mmol) at 0° C. then heated to reflux (20 min). The solvent was removed in vacuo and submitted to SGC (SiO$_2$, 6 cm×20 cm, 15% EtOAc-hexane) affording desired product and some decarboxylated material.

$^1$H NMR (CDCl$_3$, 300 MHz) consistent with assigned structure.

FABLRMS m/e 272.22 g/mole (M$^+$+H, C$_{16}$H$_{17}$NO$_3$=272 g/mole.)

EXAMPLE 10

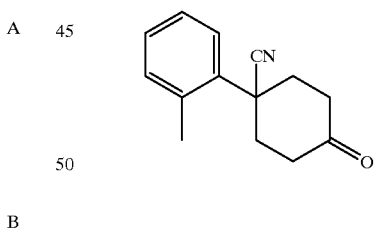

4-cyano(2-methylphenyl)-cyclohexan-1-one

A solution of the ketoester (5.0 g, 18.4 mmol) in AcOH (100 mL) was treated with 10% aqueous H$_2$SO$_4$ (10 mL) at 0° C. then heated to reflux (24 h). The solvent was removed in vacuo, diluted with EtOAc (100 mL) and water (100 mL), partitioned, washed with brine (75 mL), dried (Na$_2$SO$_4$), filtered and concentrated in vacuo and submitted to SGC (SiO$_2$, 5 cm×20 cm, 0–15% EtOAc-hexane) affording the ketone.

$^1$H NMR (CDCl$_3$, 300 MHz) 7.24 (m, 4H, ArH), 2.95 (ddd, 1 H, CHCN), 2.70 (s, 3 H, Me), 2.60 (m, 4 H), 2.20 (ddd, 2 H).

EXAMPLE 11

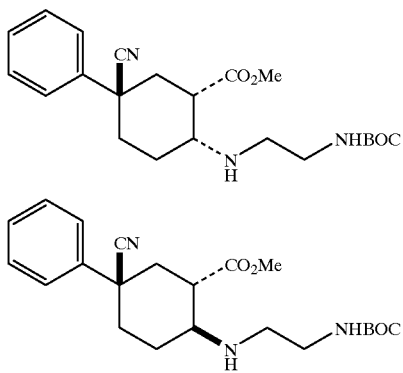

2-(2-tert-butoxycarbonylamino-ethylamino)-5-cyano-5-o-tolyl-cyclohexanecarboxylic acid methyl ester A solution of the ketoester (0.8 g, 3.75 mmol), amine (0.601 g, 3.75) and acetic acid (0.236 g, 18.75 mmol) in MeOH (10 mL) was treated with $NaBH_3CN$ (0.236 g, 3.75 mmol) at room temperature (12 h). The solvent was removed in vacuo, diluted with DCM (25 mL) and saturated aqueous sodium bicarbonate (25 mL), partitioned, extracted with DCM (2×25 mL), washed with saturated aqueous sodium bicarbonate (2×25 mL) and brine (50 mL), dried ($Na_2SO_4$), filtered and concentrated in vacuo and submitted to PCTLC ($SiO_2$, 4 mm, 90/10/1 $CHCl_3$—MeOH—$NH_4OH$) the titled trans (A) and cis (B) amines.

B $^1$H NMR ($CDCl_3$, 400 MHz) 7.24 (m, 4 H, ArH), 4.98 (br s, 1 H, NHBOC), 3.75 (s, 3 H, OMe), 3.18 (br d, 2 H, 2.89 (br ddd, 2 H), 2.80 (ddd,1 H), 2.68 (m, 1 H), 2.64 (s, 3 H, Me), 2.54 (ddd, 1 H), 2.45 (ddd, 1 H), 2.29 (ddd, 1 H), 2.01 (dd, 1 H), 1.84 (ddd, 1 H), 1.75 (ddd, 1H), 1.45 (s, 9 H, $C(Me)_3$)

EXAMPLE 12

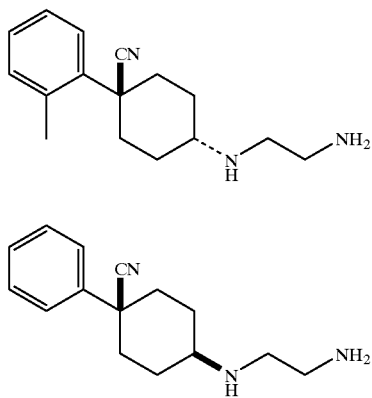

[2-(4-cyano-4-o-tolyl-cyclohexylamino)-ethyl]-carbamic acid tert-butyl ester

A solution of the ketone (0.6 g, 2.813 mmol), ethylene diamine (0.845 g, 14.1 mmol) and p-toluene sulphonic acid (0.026 g, 0.141 mmol) in benzene (10 mL) was refluxed under a Dean-Stark trap until cessation of water azeotrope. The solvent was removed in vacuo, diluted with MeOH (25 mL) and treated with $NaBH_3CN$ (0.159 g, 2.55 mmol) at room temperature (1 h). The solvent was removed in vacuo, diluted with DCM 25 mL) and saturated aqueous sodium bicarbonate (25 mL), partitioned, extracted with DCM (2×25 mL), washed with saturated aqueous sodium bicarbonate (2×25 mL) and brine (50 mL), dried ($Na_2SO_4$), filtered and concentrated in vacuo and submitted to PCTLC ($SiO_2$, 2 cm, 80/20/2 $CHCl_3$—MeOH—$NH_4OH$) the titled trans (minor) (A) and cis (major) (B) amines.

A trans: $^1$H NMR ($CDCl_3$, 300 MHz) 7.38 (m, 1 H), 7.20 (m, 3 H, ArH), 2.98 (br m, 1 H, CHNH), 2.80 (br t, 2 H), 2.65 (s, 3 H, Me), 2.64 (br m, 2 H), 2.38 (br dd, 2 H) 2.09 (br m, 4 H), 1.83 (br d, 2 H).

B cis: $^1$H NMR ($CDCl_3$,300 MHz) 7.24 (m, 4 H, ArH), 2.83 (br dd, 2 H), 2.75 (br dd, 2 H), 2.65 (s, 3 H, Me), 2.55 (br m, 1 H, CHNH), 2.43 (br m, 2 H), 2.16 (br d, 2 H), 1.67 (br d, 4 H).

EXAMPLE 13

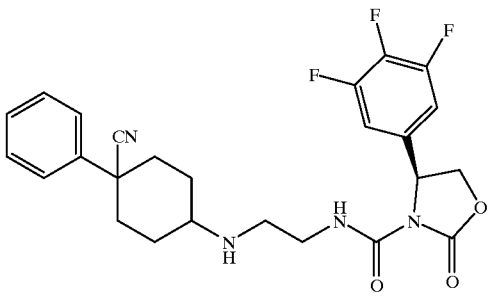

(+)-2-Oxo-4-(3,4,5-trifluorophenyl)-oxazolidine-3-carboxylic acid [2-(4-cyano-4-phenyl-cyclohexylamino)-ethyl]amide To a solution of 1-[(2-amino-ethyl)-amino]-4-cyano-4-phenylhexane (25 mg, 0.103 mmol) in 10 mL of THF, 4-(3,4,5-trifluorophenyl)-2-oxo-oxazolidine-3-carboxylic acid-4-nitro-phenyl ester (30 mg, 0.079 mmol) was added and the resulting yellow solution was stirred under argon atmosphere for 2 h at room temperature. The solvent was removed in vacuo and the residue was purified by column chromatography over silica gel with 1:1 hexane/EtOAc followed by MeOH:EtOAc=1:9 ($R_f$=0.60, MeOH:EtOAc= 1:3) to obtain the title compound. The compound was dissolved in $CH_2Cl_2$ (3 mL) and was treated with 1N HCl in ether (1 mL). The solvent was removed in vacuo to give the corresponding hydrochloride salt as a pale yellow solid. M. P. 130–134° C.; $[\alpha]_D$=+43.5, (c=0.25, MeOH); Anal. Calcd. For $C_{25}H_{26}N_4O_3F_3Cl$ 1.10 $C_3H_6O$: C, 57.92; H, 5.60; N, 8.55. Found: C, 58.33; H, 5.90; N, 8.52.

EXAMPLES 14 AND 15

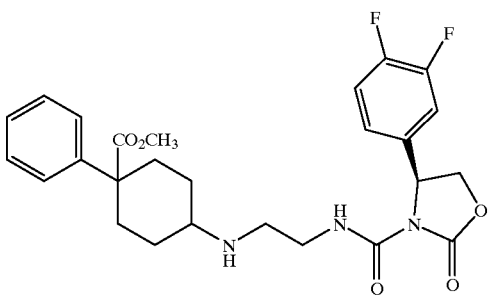

(+)-2-Oxo-4-(3,4-difluorophenyl)-oxazolidine-3-carboxylic acid [2-(4-phenyl-4-methoxycarbonyl-cyclohexylamino)-ethyl]amide (cis isomer) and (+)-2-Oxo-4-(3,4-difluorophenyl)-oxazolidine-3-carboxylic acid [2-(4-phenyl-4-methoxycarbonyl-cyclohexylamino)-ethyl]amide (trans isomer)

a. 2-[4-Cyano-4-phenylcyclohex-1-yl]aminoethylamine

A mixture of 4-cyano-4-phenylcyclohexanone (48.7 mmol) and ethylenediamine (8.78 g, 146 mmol) and p-toluenesulfonic acid (92 mg) in benzene (200 mL) was refluxed for 4 h in Dean-Stark trap to remove the water that formed. Solvent was evaporated and the residue was redissolved in methanol (60 mL) and cooled to 0 C. To this, sodium borohydride (6.4 5 g) was added in portions and the mixture was stirred at room temperature for 3 h. Solvent was evaporated, the residue was dissolved in dichloromethane (300 mL), washed with brine (3×500 mL), dried (potassium carbonate), and the solvent evaporated to leave the product as a pale yellow viscous oil (90–95%). The $^1$H-NMR showed the product to be pure and found to contain the cis/trans isomers in the ratio of about 9:1. A careful chromatography of this mixture with chloroform/methanol/2M ammonia in methanol (100/10/5 to 100/20/10) gave some earlier fractions enriched in the trans isomer relative to the amino and cyano groups. The fractions eluted at the end were almost pure cis isomer relative to the amino and cyano groups.

b. 2-[4-Methoxycarbonyl-4-phenylcyclohex-1-yl]aminoethylamine

A mixture of 2-[4-cyano-4-phenylcyclohex-1-yl]aminoethylamine (2.34 g, 10 mmol) and concentrated sulfuric acid (20 mL) was heated at 80–85° C. for 10 h. It was cooled to room temperature, mixed with anhydrous methanol (200 mL), and refluxed for 20 h. Solvent was evaporated and the residue was poured onto ice (200 g) and basified to pH 11 by addition 6N NaOH. It was extracted with dichloromethane (4×125 mL), dried (potassium carbonate) and solvent evaporated to leave the product as an oil (2.1 g, 76%). $^1$H-NMR showed this product to be pure and a mixture of cis and trans isomers. It was used in the next step without any further purification.

c. (+)-2-Oxo-4-(3,4-difluorophenyl)-oxazolidine-3-carboxylic acid [2-(4-phenyl-4-methoxycarbonyl-cyclohexylamino)-ethyl]amide (cis isomer) and (+)-2-Oxo-4-(3,4-difluorophenyl)-oxazolidine-3-carboxylic acid [2-(4-phenyl-4-methoxycarbonyl-cyclohexylamino)-ethyl]amide (trans isomer).

A mixture of 4-(3,4-difluorophenyl)-3-(4-nitrophenyloxy-carbonyl)-2-oxo-oxazolidine (50 mg, 0.123 mmol) and 2-[4-methoxy-carbonyl-4-phenylcyclohex-1-yl] aminoethylamine (75 mg) in dichloromethane (6 mL) was stirred at room temperature and the product formed was purified by preparative TLC on silica gel using ethyl acetate as the eluent. There were two bands for the two isomers, the higher band was the minor product ($^1$H-NMR confirmed it to be the cis isomer with respect to methoxycarbonyl and amine groups) and the lower band was the major product ($^1$H-NMR confirmed it to be the trans isomer with respect to methoxycarbonyl and amine groups). The HCl salt was made by treatment with 1N HCl in ether.

(+)-2-Oxo-4-(3,4-difluorophenyl)-oxazolidine-3-carboxylic acid [2-(4-phenyl-4-methoxycarbonyl-cyclohexylamino)-ethyl]amide (cis isomer). $[\alpha]_D$=65.8 (c=0.50 g, methanol); m.p. 146–148 C; Anal. Calcd. For: $C_{26}H_{29}F_2N_3O_5$.HCl: C, 58.05; H, 5.62; N, 7.81. Found: C, 58.45; H, 5.51; N, 7.89.

(+)-2-Oxo-4-(3,4-difluorophenyl)-oxazolidine-3-carboxylic acid [2-(4-phenyl-4-methoxycarbonyl-cyclohexylamino)-ethyl]amide (trans isomer). $[\alpha]D$ =+66 (c=0.48 g, methanol); m.p. 140–142 C; Anal. Calcd. For: $C26H_{29}F_2N_3O_5$. HCl.0.4H$_2$O: C, 57.16; H, 5.39; N, 7.61. Found: C, 57.28; H, 5.69; N, 7.79.

EXAMPLE 16

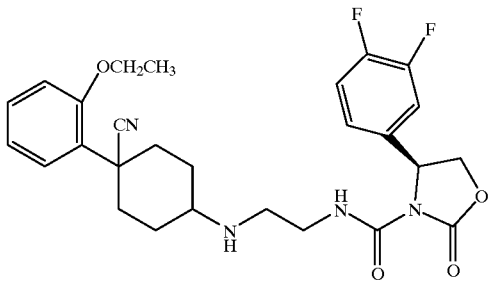

(+)-cis-2-Oxo-4-(3,4-difluorophenyl)-oxazolidine-3-carboxylic acid [2-(4-cyano-4-(2-ethoxyphenyl)-cyclohexylamino)-ethyl]amide a. 4-Cyano-4-(2-ethoxy)phenyl-2-methoxycarbonylcyclohexanone A solution of 40% methanolic triton-B (1.8 mL) in t-butyl alcohol (3.7 mL) was slowly added to a solution of 2-ethoxybenzyl cyanide (3.0 g, 18.6 mmol) and methyl acrylate (5.4 mL, 60.0 mmol) in refluxing t-butyl alcohol (5.4 mL). The mixture, after having been heated at reflux overnight, was concentrated. The residue was dissolved in chloroform (50 mL) and washed with 2N HCl (40 mL) and water (40 mL), dried (Na$_2$SO$_4$), filtered and concentrated to give a colorless oil (5.98 g, 96%). This oil (5.98 g, 17.9 mmol) was dissolved in dry toluene (50 mL), cooled by an ice water bath and treated with NaH (60% oil dispersion, 804 mg, 20.1 mmol). The mixture was heated at reflux for 4 h. A solution of 2N acetic acid (21 mL) was added. The organic layer was separated, washed with NaHCO$_3$ solution, dried (Na$_2$SO$_4$), filtered and concentrated to give a light brown liquid (4.76 g). It was dissolved in CH$_2$Cl$_2$ and flash chromatographed over silica gel (320 g) eluting with EtOAc/hexane (1:10) to afford a white solid (2.09 g, 39%): mp 82–88 C.; ESMS m/e=302 (MH$^+$).

b. 4-Cyano-4-(2-ethoxy)phenylcyclohexanone

4-Cyano-4-(2-ethoxy)phenyl-2-methoxycarbonylcyclohexanone (1.06 g, 3.5 mmol) was heated at reflux in acetic acid (24 mL) and 10% H$_2$SO$_4$ (13 mL) for 6 h. Extraction with benzene (3×10 mL), which was washed with K$_2$CO$_3$ solution, dried (Na$_2$SO$_4$), filtered and concentrated, gave a white solid (0.755 g, 88%): mp 116–121 C.

c. cis-4-Cyano-4-(2-ethoxy)phenylcyclohexyl-aminoethylamine

4-Cyano-4-(2-ethoxy)phenylcyclohexanone (300 mg, 1.23 mmol) was mixed with ethylenediamine (420 mL, 6.28 mmol) and a catalytic amount of tosic acid monohydrate in benzene (10 mL) and heated at reflux for 6 h. The solvent was evaporated off and the residue dissolved in dry EtOH (10 mL). After treatment with $NaBH_4$ (47 mg, 1.24 mmol), the mixture was stirred at room temperature for 3 h. The solvent was evaporated off and the residue triturated with $CH_2Cl_2$, treated with anhydrous $Na_2SO_4$ and filtered to afford a pale yellow oil (320 mg, 90%).

d. (+)-cis-2-Oxo-4-(3,4-difluorophenyl)-oxazolidine-3-carboxylic acid [2-(4-cyano-4-(2-ethoxyphenyl)-cyclohexylamino)-ethyl]amide To cis-4-cyano-4-(2-ethoxy)phenylcyclohexylaminoethylamine (43 mg, 0.15 mmol) in dry THF (5 mL) was added (+)-4-(3,4-difluoro)phenyl-3-(4-nitro)phenoxycarbonyl-2-oxazolidone (50 mg, 0.14 mmol). The yellow solution was stirred at room temperature for 5 h before it was concentrated. The residue was dissolved in $CHCl_3$ and flash chromatographed over silica gel (18 g) eluting with EtOAc/hexane (1:1) and then EtOAc/2M $NH_3$ in MeOH (20:1) to give a colorless oil (41 mg, 58%). It was dissolved in $CHCl_3/CH_2Cl_2$ and treated with 1M HCl in ether (120 μL) to afford a white solid: mp 125 C. (dec.); $[α]_D$=71.4 (2.1 mg/mL MeOH); ESMS m/e=513 (MH$^+$). Anal. Calcd. for $C_{27}H_{30}F_2N_4O_4 \cdot HCl \cdot 0.5CHCl_3$: C, 54.26; H, 5.22; N, 9.20. Found: C, 53.98; H, 5.04; N, 8.89.

EXAMPLE 17

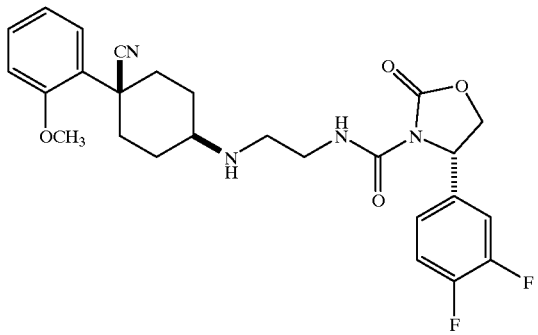

[4-cyano-4-(2-methoxy-phenyl)-cyclohexyl]-(2-{[4-(3,4-difluoro-phenyl)-2-oxo-oxazolidine-3-carbonyl]-amino}-ethyl)-ammonium chloride To a solution of dry tetrahydrofuran (2 mL) containing 120 mg (0.33 mmole) of (+)-4-(3,4-difluorophenyl)-2-oxo-oxazolidine-3-carboxylic acid 4-nitrophenyl ester was added 87 mg (0.32 mmole) of 2-{[4-cyano-4-(2-methoxy)phenyl]cyclohexylamino}ethyl amine at ambient temperature under argon. The reaction mixture was stirred for 15 minutes and then was treated with 5 mL of 10% potassium carbonate solution. The reaction mixture was extracted with ethyl acetate (2×). The combined organic extracts were washed with brine, dried (sodium sulfate) and concentrated to give the crude product as an oil. Column chromatography of the reaction product on silica gel (methanol/methylene chloride gradient elution (1 to 4%)) afforded the title compound which was converted to its salt form with HCl in dioxane: m.p. 140° C. (d);

HPLC=>99% pure at 215 nm

NMR($CDCl_3$, 400 MHz): Consistent with structure assignment and confirms presence of solvent.

FAB MS: 499 (M$^+$+1).

Analysis for $C_{26}H_{28}F_2N_4O_4 \cdot HCl \cdot 0.3H_2O$: Calculated: C, 57.79; H, 5.52; N, 10.37. Found: C, 57.76; H, 5.80; N, 10.47.

EXAMPLE 18

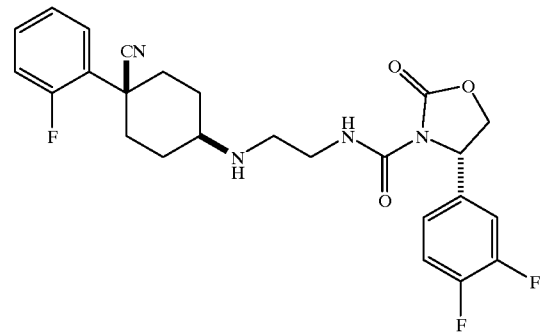

[4-cyano-4-(2-fluoro-phenyl)-cyclohexyl]-(2-{[4-(3,4-difluoro-phenyl)-2-oxo-oxazolidine-3-carbonyl]-amino}-ethyl)-ammonium chloride Using reaction conditions identical to those described in Example 19,139 mg (0.38 mmole) of (+)-4-(3,4-difluorophenyl)-2-oxo-oxazolidine-3-carboxylic acid 4-nitrophenyl ester in 2 mL of tetrahydrofuran was converted to the title compound by reacting it with 100 mg (0.38 mmole) of 2-{[4-cyano-4-(2-fluoro)phenyl]cyclohexylamino}ethyl. The chromatographed product was converted to the HCl salt and lyophilized:

HPLC=>99% pure at 215 nm

NMR($CDCl_3$, 400 MHz): Consistent with structure assignment and confirms presence of solvent.

FAB MS: 487 (M$^+$+1).

Analysis for $C_{25}H_{25}F_3N_4O_2 \cdot HCl \cdot 0.6H_2O$: Calculated: C, 56.25; H, 5.14; N, 10.50. Found: C, 56.21; H, 4.74; N, 10.27.

EXAMPLE 19

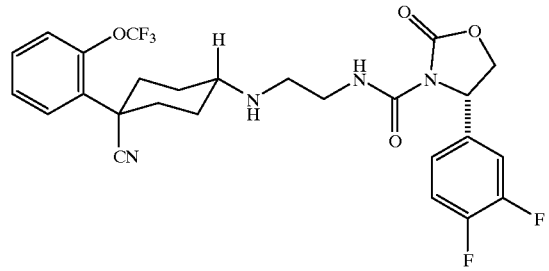

4-(3,4-difluoro-phenyl)-2-oxo-oxazolidine-3-carboxylic acid {2-[4-cyano-4-(2-trifluoromethoxy-phenyl)-cyclohexylamino]-ethyl}-amide To a solution of dry N,N-dimethylformamide (5 mL) containing 137 mg (0.34 mmole) of 2-{[4-cyano-4-(2-trifluoromethoxy)phenyl]cyclohexylamino}ethyl amine hydrochloride was added 124 mg (0.34 mmole) of (+)-4-(3,4-difluorophenyl)-2-oxo-oxazolidine-3-carboxylic acid 4-nitrophenyl ester and 124 μL (1.2 mmole) of diisopropylethylamine at ambient temperature. The homogeneous reaction mixture was stirred for 30 minutes, concentrated in vacuo and and residue was dissolved in ethyl acetate. The ethyl acetate solution was washed with 10% potassium carbonate solution (6×), dried (magnesium sulfate) and concentrated to give the crude product as an oil. Flash column chromatography of the reaction product on silica gel (methanol/methylene chloride/ammonium hydroxide, gradient elution (0.5 to 2%)) afforded the title compound in analytically pure form:

HPLC=96% pure at 215 nm

NMR(CDCl$_3$, 400 MHz): Consistent with structure assignment and confirms presence of solvent.

FAB MS: 553 (M$^+$+1).

Analysis for $C_{26}H_{25}F_5N_4O_4 \cdot 0.55H_2O$: Calculated: C, 55.52; H, 4.68; N, 9.96. Found: C, 55.54; H, 4.64; N, 10.01.

EXAMPLE 20

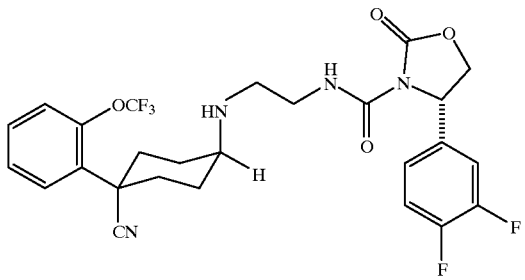

4-(3,4-difluoro-phenyl)-2-oxo-oxazolidine-3-carboxylic acid {2-[4-cyano-4-(2-trifluoromethoxy-phenyl)-cyclohexylamino]-ethyl}-amide Using reaction conditions identical to those described in Example 21, 126 mg (0.35 mmole) of (+)-4-(3,4-difluorophenyl)-2-oxo-oxazolidine-3-carboxylic acid 4-nitrophenyl ester in 5 mL of N,N-dimethylformamide was converted to the title compound with 139 mg (0.35 mmole) of 2-{[4-cyano-4-(2-trifluoromethoxy)phenyl]cyclohexylamino}ethyl amine hydrochloride and 211 μL (1.2 mmole) of diisopropylethylamine. Extractive workup, followed by flash chromatography of the crude reaction product, and lyophilization gave a white solid:

HPLC=>99% pure at 215 nm

NMR(CDCl$_3$, 400 MHz): Consistent with structure assignment.

FAB MS: 553 (M$^+$+1).

Analysis for $C_{26}H_{25}F_5N_4O_4$: Calculated: C, 56.52; H, 4.56; N, 10.14. Found: C, 56.76; H, 4.72; N, 10.18.

EXAMPLE 21

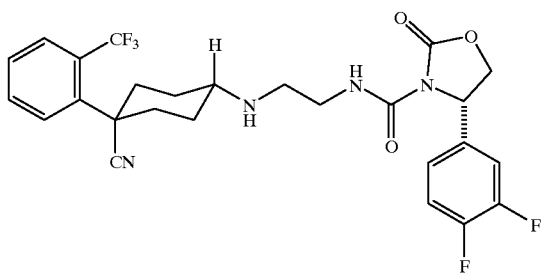

4-(3,4-difluoro-phenyl)-2-oxo-oxazolidine-3-carboxylic acid (2-[4-cyano-4-(2-trifluoromethyl-phenyl)-cyclohexylamino]-ethyl}-amide Using reaction conditions identical to those described in Example 21, 122 mg (0.34 mmole) of (+)-4-(3,4-difluorophenyl)-2-oxo-oxazolidine-3-carboxylic acid 4-nitrophenyl ester in 5 mL of N,N-dimethylformamide was converted to the title compound by reacting it with 129 mg (0.34 mmole) of 2-{[4-cyano-4-(2-trifluoromethyl)phenyl]cyclohexylamino}ethyl amine hydrochloride and 204 μL (1.2 mmole) of diisopropylethylamine. Extractive workup, followed by flash chromatography of the crude reaction product, and lyophilization gave the title compound as a white powder:

HPLC=99% pure at 215 nm

NMR(CDCl$_3$, 400 MHz): Consistent with structure assignment.

FAB MS: 537 (M$^+$+1).

Analysis for $C_{26}H_{25}F_5N_4O_3$: Calculated: C, 58.21; H, 4.70; N, 10.44. Found: C, 57.70; H, 4.55; N, 10.32.

EXAMPLE 22

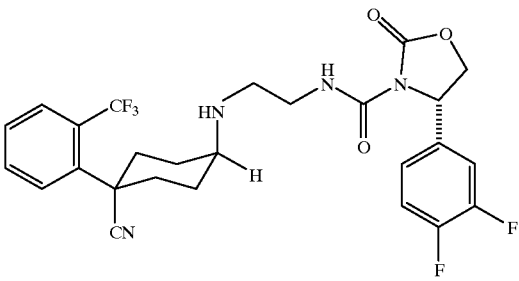

4-(3,4-difluoro-phenyl)-2-oxo-oxazolidine-3-carboxylic acid {2-[4-cyano-4-(2-trifluoromethyl-phenyl)-cyclohexylamino]-ethyl}-amide Using reaction conditions identical to those described in Example 21, 130 mg (0.36 mmole) of (+)-4-(3,4-difluorophenyl)-2-oxo-oxazolidine-3-carboxylic acid 4-nitrophenyl ester in 5 mL of N,N-dimethylformamide was converted to the title compound by reacting it with 138 mg (0.36 mmole) of 2-{[4-cyano-4-(2-trifluoromethyl)phenyl]cyclohexylamino}ethyl amine hydrochloride and 219 μL (1.26 mmole) of diisopropylethylamine. Extractive workup, followed by flash chromatography of the crude reaction product, and lyophilization gave the title compound as a white powder:

HPLC=97% pure at 215 nm

NMR(CDCl$_3$, 400 MHz): Consistent with structure assignment.

FAB MS: 537 (M$^+$+1).

Analysis for C$_{26}$H$_{25}$F$_5$N$_4$O$_3$: Calculated: C, 58.21; H, 4.70; N, 10.44. Found: C, 57.80; H, 4.61; N, 10.42.

EXAMPLE 23

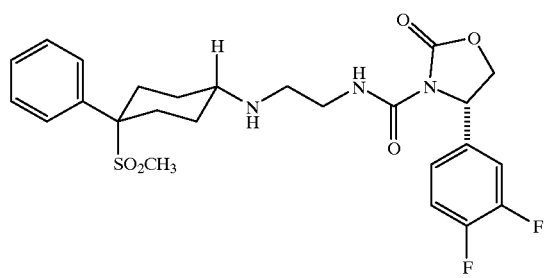

(2-{[4-(3,4-difluoro-phenyl)-2-oxo-oxazolidine-3-carbonyl]-amino}-ethyl)-(4-methanesulfonyl-4-phenyl-cyclohexyl)-ammonium chloride Using reaction conditions identical to those described in Example 21, 172 mg (0.47 mmole) of (+)-4-(3,4-difluorophenyl)-2-oxo-oxazolidine-3-carboxylic acid 4-nitrophenyl ester in a solvent mix of 8 mL of N,N-dimethylformamide and 2 mL of tetrahydrofuran was converted to the title compound by reacting it with 175 mg (0.47 mmole) of 2-[(4-methansulfonyl-4-phenyl)cyclohexylamino]ethyl amine hydrochloride and 288 μL (1.66 mmole) of diisopropylethylamine. Extractive workup, followed by flash chromatography of the crude reaction product (silica gel; methanol/methylene chloride elution, 1:1), and lyophilization gave the title compound which was converted to its HCl salt with HCl in dioxane:

HPLC=>93% pure at 215 nm

NMR(CDCl$_3$, 400 MHz): Consistent with structure assignment and confirms presence of solvent.

FAB MS: 522 (M$^+$+1).

Analysis for C$_{25}$H$_{29}$F$_2$N$_3$O$_5$S.0.95 H$_2$O: Calculated: C, 52.20; H, 5.59; N, 7.31. Found: C, 52.19; H, 5.28; N, 7.22.

EXAMPLE 24

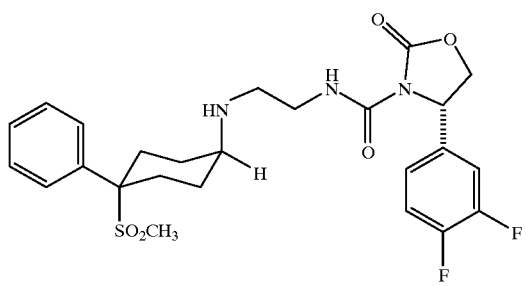

(2-{[4-(3,4-difluoro-phenyl)-2-oxo-oxazolidine-3-carbonyl]-amino}-ethyl)-(4-methanesulfonyl-4-phenyl-cyclohexyl)-ammonium chloride Using reaction conditions identical to those described in Example 21, 153 mg (0.42 mmole) of (+)-4-(3,4-difluorophenyl)-2-oxo-oxazolidine-3-carboxylic acid 4-nitrophenyl ester in 2 mL of N,N-dimethylformamide was converted to the title compound by reacting it with 155 mg (0.42 mmole) of 2-[(4-methansulfonyl-4-phenyl) cyclohexylamino]ethyl amine hydrochloride and 256 μL (1.47 mmole) of diisopropylethylamine. Extractive workup, followed by flash chromatography of the crude reaction product (silica gel; methanol/methylene chloride/ ammonium hydroxide gradient elution), and lyophilization gave the title compound which was converted to its 4HCl salt with HCl in dioxane:

HPLC=>93% pure at 215 nm

NMR(CDCl$_3$, 400 MHz): Consistent with structure assignment and confirms presence of solvent.

FAB MS: 522 (M$^+$+1).

Analysis for C$_{25}$H$_{29}$F$_2$N$_3$O$_5$S.0.5 H$_2$O: Calculated: C, 52.95; H, 5.51; N, 7.41. Found: C, 53.14; H, 5.80; N, 7.02.

Utilizing the methodology described in detail in the Examples and schemes above, the following compounds shown in Table 1 were made.

TABLE 1

| R$^2$ | Q | cis/trans | FABLRMS | HPLC R.T. | Elemental Analysis |
|---|---|---|---|---|---|
| CBZ$^4$ | (isobutyl-phenyl-difluoro amide group) | cis | 574.27 g/mole | 14.19 min. | Calc. for 0.95 H$_2$O; 0.25 EtOAc Solvate mol. wt. = 612.83 g/mole Calc: C = 68.60% H = 6.73% N = 6.86% Obs: C = 69.52% H = 6.31% N = 6.95% |

TABLE 1-continued
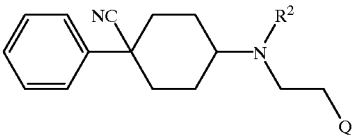
| R² | Q | cis/trans | FABLRMS | HPLC R.T. | Elemental Analysis |
|---|---|---|---|---|---|
| 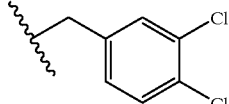 | 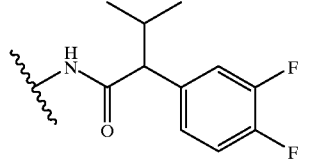 | cis | 598.32 g/mole | 12.49 min. | N/A |
| H | 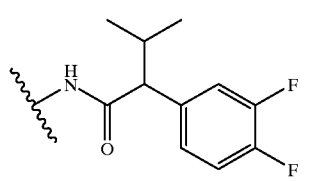 | cis (±) | 440.30 g/mole | 9.72 min. | N/A |
|  | 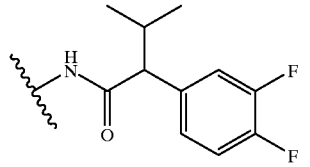 | cis | 482.41 g/mole | 10.44 min. | N/A |
| 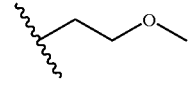 | 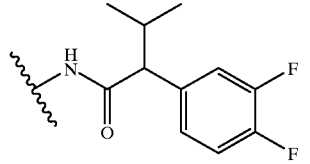 | cis | 498.31 g/mole | 10.21 min. | Calc. for 0.10 H₂O; 0.60 CHCl₃ Solvate mol. wt. = 571.06 g/mole Calc.: C = 62.26% H = 6.67% N = 7.36% Obs.: C = 62.22% H = 6.54% N = 7.08% |
| H | 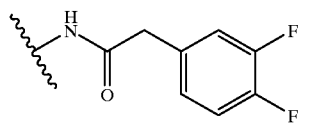 | cis | 398.28 g/mole | 8.00 min. | Calc. for 0.30 H₂O; 1.0 HCl Solvate mol. wt. = 487.08 g/mole Calc.: C = 62.26% H = 6.67% N = 7.36% Obs.: C = 62.22% H = 6.54% N = 7.08% |
| 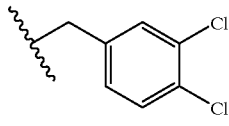 | 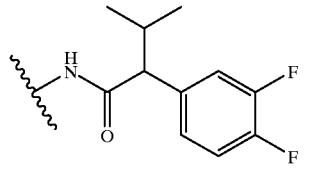 | cis | 598.23 g/mole | 12.49 min. | N/A |
| H | 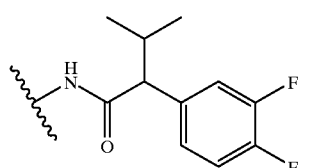 | cis (±) | 440.30 g/mole | 9.72 min. | N/A |

TABLE 1-continued

| R² | Q | cis/trans | FABLRMS | HPLC R.T. | Elemental Analysis |
|---|---|---|---|---|---|
| isopropyl | α-isopropyl-(3,4-difluorophenyl)acetamide | cis | 482.41 g/mole | 10.44 min. | N/A |
| H | 3,4-difluorobenzamide | cis | 384.21 g/mole | 8.08 min. | Calc. for 0.20 MeOH; 1.0 HCl<br>Solvate mol. wt. = 426.32 g/mole<br>Calc.: C = 62.55% H = 5.86% N = 9.86%<br>Obs.: C = 62.53% H = 5.83% N = 9.62% |
| H | 2,2-dicyclopropylacetamide | cis | 366.27 g/mole | 8.17 min. | Calc. for 0.85 H₂O; 1.0 HCl; 0.25 EtOAc<br>Solvate mol. wt. = 439.82 g/mole<br>Calc.: C = 65.54% H = 8.19% N = 9.56%<br>Obs.: C = 65.54% H = 7.86% N = 9.58% |
| H | 9-hydroxy-9H-fluorene-9-carboxamide | cis | 452.23 g/mole | 8.23 min. | Calc. for 0.20 H₂O;<br>Solvate mol. wt. = 456.09 g/mole<br>Calc.: C = 76.53% H = 6.51% N = 9.23%<br>Obs.: C = 76.64% H = 6.51% N = 9.31% |
| H | —NH₂ | cis | N/A | 5.54 min. | Calc. for 0.40 H₂O; 2.0 HCl; 0.30 MeOH<br>Solvate mol. wt. = 333.10 g/mole<br>Calc.: C = 55.17% H = 7.57%<br>N = 12.62%<br>Obs.: C = 55.27% H = 7.36%<br>N = 12.63% |
| acetyl | acetamide | cis | 328.35 g/mole | 7.33 min. | Calc.: C = 69.48%<br>H = 7.98% N = 12.79%<br>Obs.: C = 69.40%<br>H = 7.53% N = 12.61% |
| H | acetamide | cis | 286.29 g/mole | 5.85 min. | Calc. for 0.65 H₂O; 0.95 EtOAc<br>Solvate mol. wt. = 417.26 g/mole<br>Calc.: C = 59.87%<br>H = 7.95% N = 10.07%<br>Obs.: C = 59.90%<br>H = 8.04% N = 10.10% |

TABLE 1-continued

| R² | Q | cis/trans | FABLRMS | HPLC R.T. | Elemental Analysis |
|---|---|---|---|---|---|
| H | (isopropyl-CH-C(O)-NH- attached to 3,4-difluorophenyl) | cis (−) | 440.25 g/mole | 9.81 min. | Calc. for 0.30 H₂O; 1.0 HCl Solvate mol. wt. = 501.49 g/mole Calc.: C = 62.99% H = 6.55% N = 8.38% Obs.: C = 63.16% H = 6.28% N = 8.83% |
| H | (isopropyl-CH-C(O)-NH- attached to 3,4-difluorophenyl) | cis (+) | 440.24 g/mole | 9.81 min. | Calc. for 0.50 H₂O; 0.85 CHCl₃; 1.0 HCl Solvate mol. wt. = 549.10 g/mole Calc.: C = 58.73% H = 6.20% N = 7.64% Obs.: C = 58.72% H = 6.15% N = 7.48% |
| CBZ⁴ | -NH-C(O)-CH₃ | cis | 378.25 g/mole | 8.89 min. | N/A |

⁴ -C(O)-O-CH₂-phenyl

EXAMPLE 25

As a specific embodiment of an oral composition, 100 mg of the compound of Example 5 is formulated with sufficient finely divided lactose to provide a total amount of 580 to 590 mg to fill a size O hard gel capsule.

EXAMPLE 26

Screening Assay: Alpha 1a Adrenergic Receptor Binding

Membranes prepared from the stably transfected human alpha 1a cell line (ATCC CRL 11140) were used to identify compounds that bind to the human alpha 1a adrenergic receptor. These competition binding reactions (total volume=200 µl) contained 50 mM Tris-HCl pH. 7.4, 5 mM EDTA, 150 mM NaCl, 100 pM [$^{125}$I]-HEAT, membranes prepared from the alpha 1a cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki). Representative compounds of the present invention were found to have Ki values ≦50 nM.

EXAMPLE 27

Selective Binding Assays

Membranes prepared from stably transfected human alpha 1d and alpha 1b cell lines (ATCC CRL 11138 and CRL 11139, respectively) were used to identify compounds that selectively bind to the human alpha 1a adrenergic receptor. These competition binding reactions (total volume=200 µl) contained 50 mM Tris-HCl pH. 7.4, 5 mM EDTA, 150 mM NaCl, 100 pM [$^{125}$I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

EXAMPLE 28

Exemplary Counterscreens

1. Assay Title: Dopamine D2, D3, D4 in vitro screen

Objective of the Assay

The objective of this assay is to eliminate agents which specifically affect binding of [3H] spiperone to cells expressing human dopamine receptors D2, D3 or D4.

Method

Modified from VanTol et al (1991); Nature (Vol 350) Pg 610–613.

Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15' at 24,450 rpm) are resuspended in 50 mM Tris-HCl pH 7.4 containing EDTA, MgCl[2], KCl, NaCl, CaCl[2] and ascorbate to give a 1 Mg/mL suspension. The assay is initiated by adding 50–75 μg membranes in a total volume of 500 μl containing 0.2 nM [3H]-spiperone. Non-specific binding is defined using 10 μM apomorphine. The assay is terminated after a 2 hour incubation at room temperature by rapid filtration over GF/B filters presoaked in 0.3% PEI, using 50 mM Tris-HCl pH 7.4.

2. Assay Title Serotonin 5HT1a

Objective of the Assay

The objective of this assay is to eliminate agents which specifically affect binding to cloned human 5HT1a receptor Method Modified from Schelegel and Peroutka *Biochemical Phamacology* 35:1943–1949 (1986).

Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000×g for 30', and then the supernatant is centrifuged again at 38,000×g for 30'. The binding assay contains 0.25 nM [3H]8-OH-DPAT (8-hydroxy-2-dipropylamino-1,2,3,4-tetrahydronaphthalene) in 50 mM Tris-HCl, 4 mM CaCl2 and 1 mg/ml ascorbate. Non-specific binding is defined using 10 μM propranolol. The assay is terminated after a 1 hour incubation at room temperature by rapid filtration over GF/Cfilters

EXAMPLE 29

Exemplary Functional Assays

In order to confirm the specificity of compounds for the human alpha 1a adrenergic receptor and to define the biological activity of the compounds, the following functional tests may be performed:

1. In vitro Rat, Dog and Human Prostate and Dog Urethra

Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% $CO_2$/95% $O_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 μM (for rat), 10 μM (for dog) and 20 μM (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.

$EC_{50}$ values are calculated for each group using GraphPad Inplot software. $pA_2$ ($-\log K_b$) values were obtained from Schild plot when three or more concentrations were tested. When less than three concentrations of antagonist are tested, $K_b$ values are calculated according to the following formula $$K_b = \frac{[B]}{x-1}$$

where x is the ratio of $EC_{50}$ of agonist in the presence and absence of antagonist and [B] is the antagonist concentration.

2. Measurement of Intra-Urethral Pressure in Anesthetized Dogs

Purpose: Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha 1 receptor antagonists which also have pronounced vascular effects. Because we have identified the alpha 1a receptor subtype as the predominent subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha 1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

Methods: Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha 1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four paramenter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha 1 antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonists that prevent the increase in intra-urethral pressure to phenylephrine without any activity at the vasculature.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of the formula:

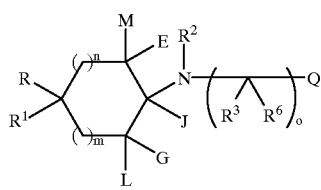

wherein Q is

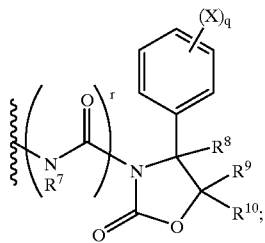

E, G, L and M are each independently hydrogen, $C_{1-8}$ alkyl, $C_{3-8}$ cycloalkyl, $(CH_2)_{0-4}OR^{15}$, $(CH_2)_{0-4}N(R^{16})_2$, $(CH_2)_{0-4}CN$, $(CH_2)_{0-4}CF_3$, $(CH_2)_{0-4}CO_2R^{16}$, $(CH_2)_{0-4}CON(R^{16})_2$, $(CH_2)_{0-4}SO_2R^{15}$ or $(CH_2)_{0-4}SO_2N(R^{16})_2$;

J is hydrogen, $C_{1-8}$ alkyl, $C_{3-8}$ cycloalkyl, $(CH_2)_{1-4}OR^{15}$, $(CH_2)_{1-4}N(R^{16})_2$, $(CH_2)_{1-4}CN$, $(CH_2)_{0-4}CF_3$, $(CH_2)_{0-4}CO_2R_{16}$, $(CH_2)_{0-4}CON(R^{16})_2$, $(CH_2)_{0-4}SO_2R^{15}$ or $(CH_2)_{0-4}SO_2N(R^{16})_2$;

$R^1$ is unsubstituted, mono- or poly-substituted phenyl wherein the substitutents on the phenyl are independently selected from halogen, $CF_3$, cyano, nitro, $N(R^{16})_2$, $NR^{16}COR^{18}$, $NR^{16}CON(R^{18})_2$, $NR^{16}SO_2R^{18}$, $NR^{16}SO_2N(R^{18})_2$, $OR^{15}$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$ and $C_{1-4}$ alkyl; or unsubstituted, mono- or poly-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, nitro, $N(R^{16})_2$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$, phenyl, $OR^{15}$, halogen, $C_{1-4}$ alkyl and $_{3-8}$ cycloalkyl;

R is hydrogen, cyano, $OR^{15}$, $CO_2R^{15}$, $CON(R^{16})_2$, $SO_2R^{15}$, $SO_2N(R^{16})_2$, tetrazole, isooxadiazole, unsubstituted, mono- or poly-substituted phenyl wherein the substitutents on the phenyl are independently selected from halogen, cyano, $OR^{15}$, $(CH_2)_{0-4}CO_2R^{16}$, $(CH_2)_{0-4}CON(R^{16})_2$, $N(R^{16})_2$, $NR^{16}COR^{15}$, $NR^{16}CON(R^{18})_2$, $NR^{16}SO_2R^{15}$, $NR^{16}SO_2N(R^{18})_2$, $(CH_2)_0SO_2N(R^{16})_2$, $(CH_2)_{0-4}SO_2R^{15}$ and $C_{1-4}$ alkyl; or unsubstituted, mono- or poly-substituted pyridyl, thienyl, furanyl or naphthyl wherein the substituents on the pyridyl, thienyl, furanyl or naphthyl are independently selected from $CF_3$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$, phenyl, $OR^{15}$, halogen, $C_{1-4}$ alkyl and $C_{3-8}$ cycloalkyl;

$R^2$ and $R^7$ are each independently hydrogen, $C_{1-8}$ alkyl, $C_{4-8}$ cycloalkyl, $(CH_2)_{0-4}CO_2R^{16}$, $(CH_2)_{0-4}CON(R^{16})_2$, $(CH_2)_{0-4}COR^{15}$, $(CH_2)_{2-4}OR^{15}$, $(CH_2)_{1-4}CF_3$, $(CH_2)_{0-4}SO_2R^{15}$, $(CH_2)_{0-4}SO_2N(R^{16})_2$ or $(CH_2)_{1-4}CN$;

$R^3$, $R^6$, $R^8$, $R^9$ and $R^{10}$ are each independently hydrogen, $C_{1-8}$ alkyl, $C_{3-8}$ cycloalkyl, $(CH_2)_{1-4}OR^{15}$ or $(CH_2)_{0-4} CF_3$;

$R^{15}$ is hydrogen, $C_{1-8}$ alkyl, $C_{3-8}$ cycloalkyl or $(CH_2)_{0-4}CF_3$;

$R^{16}$ and $R^{18}$ are each independently hydrogen, $C_{1-8}$ alkyl, $C_{3-8}$ cycloalkyl or $(CH_2)_{1-4}CF_3$;

each X is independently halogen, cyano, nitro, $C_{1-8}$ alkyl, $C_{3-8}$ cycloalkyl, $(CH_2)_{0-4}OR^{24}$ or $(CH_2)_{0-4}CF_3$;

$R^{24}$ is hydrogen, $C_{1-8}$ alkyl, $C_{3-8}$ cycloalkyl or $(CH_2)_{0-4}CF_3$;

m, n and q are each independently an integer from zero to four;

o is an integer from one to four;

r is zero or one;

or a pharmaceutically acceptable salt thereof.

2. The compound of claim 1, of the formula

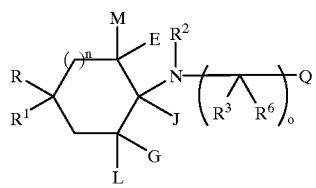

wherein

E, G, L, M and J are each independently hydrogen, $C_{1-8}$ alkyl, $C_{3-8}$ cycloalkyl, $(CH_2)_{0-4}CO_2R^{16}$ or $(CH_2)_{0-4}CF_3$;

$R^1$ is unsubstituted, mono-, di- or tri-substituted phenyl wherein the substitutents on the phenyl are independently selected from halogen, $CF_3$, cyano, nitro, $N(R^{16})_2$, $NR^{16}COR^{18}$, $NR^{16}CON(R^{18})_2$, $NR^{16}SO_2R^{18}$, $NR^{16}SO_2N(R^{18})_2$, $OR^{15}$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2(R^{15})_2$ and $C_{1-4}$ alkyl; or unsubstituted, mono-, di- or tri-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, nitro, $N(R^{16})_2$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2(R^{15})_2$, phenyl, $OR^{15}$, halogen, $C_{1-4}$ alkyl and $C_{3-8}$ cycloalkyl;

R is hydrogen, cyano, $OR^{15}$, $CO_2R^{15}$, $CON(R^{16})_2$, $SO_2R^{15}$, $SO_2N(R^{16})_2$ or unsubstituted, mono- or di-substituted phenyl wherein the substitutents on the phenyl are independently selected from halogen, cyano, $OR^{15}$, $(CH_2)_{0-4}CO_2R^{16}$, $(CH_2)_{0-4}CON(R^{16})_2$, $N(R^{16})_2$, $NR^{16}COR^{15}$, $NR^{16}CON(R^{18})_2$, $NR^{16}SO_2R^{15}$, $NR^{16}SO_2N(R^{18})_2$, $(CH_2)_{0-4}SO_2N(R^{16})_2$, $(CH_2)_{0-4}SO_2R^{15}$ and $C_{1-4}$ alkyl; or unsubstituted, mono- or di-substituted pyridyl, thienyl, furanyl or naphthyl wherein the substituents on the pyridyl, thienyl, furanyl or naphthyl are independently selected from $CF_3$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$, phenyl, $OR^{15}$, halogen, $C_{1-4}$ alkyl and $C_{3-8}$ cycloalkyl;

$R^2$ and $R^7$ are each independently hydrogen, $C_{1-8}$ alkyl, $C_{4-8}$ cycloalkyl or $(CH_2)_{1-4}CF_3$;

n is an integer from zero to two; and o is an integer from one to four;

or a pharmaceutically acceptable salt thereof.

3. The compound of claim 2, of the formula

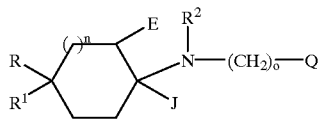

wherein Q is

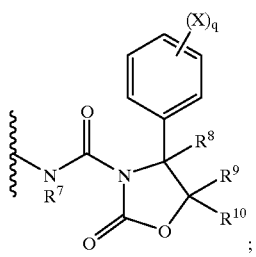

E and J are each independently hydrogen or $CO_2-C_{1-6}$ alkyl;

$R^1$ is unsubstituted, mono-, di- or tri-substituted phenyl wherein the substitutents on the phenyl are independently selected from halogen, $CF_3$, cyano, nitro, $N(R^{16})_2$, $OR^{15}$, $(CH_2)_{0-2}CO_2R^{16}$, $(CH_2)_{0-2}CON(R^{16})_2$ and $C_{1-4}$ alkyl; or unsubstituted, mono- or di-substituted pyridyl wherein the substitutents on the pyridyl are independently selected from halogen, $CF_3$, cyano, nitro, $N(R^{16})_2$, $OR^{15}$, $(CH_2)_{0-2}CO_2R^{16}$, $(CH_2)_{0-2}CON(R^{16})_2$ and $C_{1-4}$ alkyl;

R is hydrogen, cyano, $OR^{15}$, $CO_2R^{15}$, $CON(R^{16})_2$, $SO_2R^{15}$ or $SO_2N(R^{16})_2$;

$R^2$ and $R^7$ are each independently hydrogen, $C_{1-6}$ alkyl, $C_{4-6}$ cycloalkyl or $(CH_2)_{1-4}CF_3$;

$R^8$, $R^9$ and $R^{10}$ are each independently hydrogen, $C_{1-6}$ alkyl, $C_{3-6}$ cycloalkyl, $(CH_2)_{2-4}OR^{15}$ or $(CH_2)_{0-2}CF_3$;

$R^{15}$ is hydrogen, $C_{1-6}$ alkyl, $C_{3-6}$ cycloalkyl or $(CH_2)_{0-2}CF_3$;

$R^{16}$ is hydrogen, $C_{1-6}$ alkyl, $C_{3-6}$ cycloalkyl or $(CH_2)_{1-2}CF_3$;

each X is independently halogen or $C_{1-4}$ alkyl, q is an integer from zero to three;

or a pharmaceutically acceptable salt thereof.

4. The compound of claim 3, of the formula

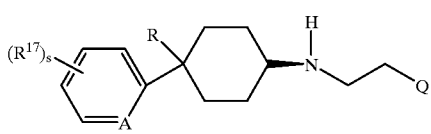

wherein Q is

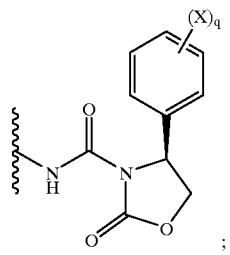

A is C—R$^{17}$ or N;

R is hydrogen, cyano, hydroxy, CO$_2$R$^{15}$, CON(R$^{16}$)$_2$, SO$_2$R$^{15}$ or SO$_2$N(R$^{16}$)$_2$;

each R$^{17}$ is independently hydrogen, halogen, CO$_2$R$^{16}$, cyano, nitro, CON(R$^{16}$)$_2$, SO$_2$R$^{15}$, SO$_2$N(R$^{16}$)$_2$ or OR$^{15}$;

each X is independently flourine or methyl; and s is an integer from zero to two;

or a pharmaceutically acceptable salt thereof.

5. The compound of claim 3, selected from
(+)-2-Oxo-4-(3,4,5-trifluorophenyl)-oxazolidine-3-carboxylic acid [2-(4-cyano-4-phenyl-cyclohexylamino)-ethyl]amide;
(+)-2-Oxo-4-(3,4-difluorophenyl)-oxazolidine-3-carboxylic acid [2-(4-phenyl-4-methoxycarbonyl-cyclohexylamino)-ethyl]amide;
(+)-cis-2-Oxo-4-(3,4-difluorophenyl)-oxazolidine-3-carboxylic acid [2-(4-Cyano-4-(2-ethoxyphenyl)-cyclohexylamino)-ethyl]amide;
[4-cyano-4-(2-methoxy-phenyl)-cyclohexyl]-(2-{[4-(3,4-difluoro-phenyl)-2-oxo-oxazolidine-3-carbonyl]-amino}-ethyl)-ammonium chloride;
[4-cyano-4-(2-fluoro-phenyl)-cyclohexyl]-(2-{[4-(3,4-difluoro-phenyl)-2-oxo-oxazolidine-3-carbonyl]-amino}-ethyl)-ammonium chloride;
4-(3,4-difluoro-phenyl)-2-oxo-oxazolidine-3-carboxylic acid {2-[4-cyano-4-(2-trifluoromethoxy-phenyl)-cyclohexylamino]-ethyl}-amide;
4-(3,4-difluoro-phenyl)-2-oxo-oxazolidine-3-carboxylic acid {2-[4-cyano-4-(2-trifluoromethoxy-phenyl)-cyclohexylamino]-ethyl}-amide;
4-(3,4-difluoro-phenyl)-2-oxo-oxazolidine-3-carboxylic acid {2-[4-cyano-4-(2-trifluoromethyl-phenyl)-cyclohexylamino]-ethyl}-amide;
4-(3,4-difluoro-phenyl)-2-oxo-oxazolidine-3-carboxylic acid {2-[4-cyano-4-(2-trifluoromethyl-phenyl)-cyclohexylamino]-ethyl}-amide;
(2-{[4-(3,4-difluoro-phenyl)-2-oxo-oxazolidine-3-carbonyl]-amino}-ethyl)-(4-methanesulfonyl-4-phenyl-cyclohexyl)-ammonium chloride; or
(2-{[4-(3,4-difluoro-phenyl)-2-oxo-oxazolidine-3-carbonyl]-amino}-ethyl)-(4-methanesulfonyl-4-phenyl-cyclohexyl)-ammonium chloride
and the pharmaceutically acceptable salts thereof.

6. A pharmaceutical composition comprising the compound of claim 1 and a pharmaceutically acceptable carrier.

7. A pharmaceutical composition made by combining a compound of claim 1 and a pharmaceutically acceptable carrier.

8. A process for making a pharmaceutical composition comprising combining a compound of claim 1 and a pharmaceutically acceptable carrier.

9. The composition of claim 6 further comprising a testosterone 5-alpha reductase inhibitor.

10. The composition of claim 9, wherein the testosterone 5-alpha reductase inhibitor is a type 1, a type 2, both a type 1 and a type 2 or a dual type 1 and type 2 testosterone 5-alpha reductase inhibitor.

11. The composition of claim 10, wherein the testosterone 5-alpha reductase inhibitor is a type 2 testosterone 5-alpha reductase inhibitor.

12. The composition of claim 11, wherein the testosterone 5-alpha reductase inhibitor is finasteride.

13. A method of treating benign prostatic hyperplasia in a subject in need thereof which comprises administering to the subject a therapeutically effective amount of the compound of claim 1.

14. The method of claim 13, wherein the compound additionally does not cause a fall in blood pressure at dosages effective to alleviate benign prostatic hyperlasia.

15. The method of claim 14, wherein the compound is administered in combination with a testosterone 5-alpha reductase inhibitor.

16. The method of claim 15, wherein the testosterone 5-alpha reductase inhibitor is finasteride.

17. A method of treating benign prostatic hyperplasia in a subject in need thereof which comprises administering a therapeutically effective amount of the composition of claim 6.

18. The method of claim 17, wherein the composition further comprises a therapeutically effective amount of a testosterone 5-alpha reductase inhibitor.

19. A method of relaxing lower urinary tract tissue in a subject in need thereof which comprises administering to the subject a therapeutically effective amount of the compound of claim 1.

20. The method of claim 19, wherein the compound additionally does not cause a fall in blood pressure at dosages effective to relax lower urinary tract tissue.

21. The method of claim 19, wherein the compound is administered in combination with a testosterone 5-alpha reductase inhibitor.

22. The method of claim 21, wherein the testosterone 5-alpha reductase inhibitor is finasteride.

23. A method of treating a condition which is susceptible to treatment by antagonism of the alpha 1a receptor which comprises administering to a subject in need thereof an amount of the compound of claim 1 effective to treat the condition.

24. A method of eliciting an alpha 1a antagonizing effect in a mammal in need thereof, comprising administering to the mammal a therapeutically effective amount of the compound of claim 1.

* * * * *